(12) United States Patent
Cereda et al.

(10) Patent No.: US 6,521,623 B1
(45) Date of Patent: Feb. 18, 2003

(54) N,N'-DISUBSTITUTED BENZIMIDAZOLONE DERIVATIVES WITH AFFINITY AT THE SEROTONIN AND DOPAMINE RECEPTORS

(75) Inventors: Enzo Cereda, Novi Ligure (IT); Luciano Maiocchi, Cernobbio (IT); Alessandro Brambilla, Milan (IT); Ettore Giraldo, Milan (IT); Eugenia Monferini, Milan (IT); Giovanni Battista Schiavi, Asola (IT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/933,598

(22) Filed: Aug. 21, 2001

Related U.S. Application Data

(60) Provisional application No. 60/250,504, filed on Dec. 1, 2000.

(30) Foreign Application Priority Data

Sep. 19, 2000 (DE) ......................... 008 30 624

(51) Int. Cl.$^7$ .................... C07D 235/26; C07D 401/12; C07D 403/12; A61K 31/4184; A61P 43/00
(52) U.S. Cl. .................. 514/252.19; 544/370; 544/364; 544/295; 514/254.06; 514/253.09; 514/292; 514/278; 514/395; 546/85; 546/20; 548/305.1
(58) Field of Search ................................ 544/370, 364, 544/295; 514/254.06, 253.09, 252.19, 292, 278, 395; 546/85, 20; 548/305.1

(56) References Cited

U.S. PATENT DOCUMENTS

| | | | |
|---|---|---|---|
| 4,200,641 A | * | 4/1980 | Vandenberk et al. ........ 424/267 |
| 5,576,318 A | | 11/1996 | Bietti et al. |
| 5,883,094 A | | 3/1999 | Fliri et al. |

FOREIGN PATENT DOCUMENTS

| | | |
|---|---|---|
| EP | 0 816 356 A1 | 7/1998 |

OTHER PUBLICATIONS

Chemical Abstract: Database Accession No. 98:16650—XP 002197885 Collino, F. et al: Mannich bases of benzimidazoles, benzotriazoles and other analogous compounds, with pharmacological activity. Database CA "Online".

* cited by examiner

Primary Examiner—Mukund J. Shah
Assistant Examiner—Hong Liu
(74) Attorney, Agent, or Firm—Robert P. Raymond; Timothy X. Witkowski; Mary-Ellen Devlin

(57) ABSTRACT

A compound of formula (I)

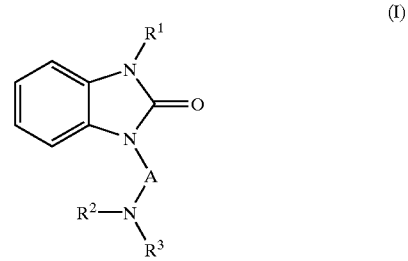

wherein:

$R^1$ is $C_1$–$C_6$-alkyl substituted by a group selected from OH, $C_1$–$C_6$-alkoxy, —OCONH$C_1$–$C_6$-alkyl, —OCON$HC_1$–$C_6$-alkyl, —NHSO$_2$$C_1$–$C_6$-alkyl, and —NHCO$C_1$–$C_6$-alkyl, or $R^1$ is $C_1$–$C_6$-alkyl substituted by a saturated or unsaturated 5- or 6-membered heterocycle containing one or two heteroatoms selected from the group consisting of nitrogen and oxygen, the heterocycle optionally substituted by a group selected from $C_1$–$C_4$-alkyl, halogen, and benzyl;

$R^2$ and $R^3$ together with the nitrogen form a saturated or unsaturated 5- or 6-membered heterocyclic ring optionally containing nitrogen or oxygen as an additional heteroatom, the heterocyclic ring thereof substituted by a group selected from phenyl, benzyl, and diphenylmethyl, each of these groups optionally mono- or di-substituted by one or two groups selected from $CF_3$, $C_1$–$C_4$-alkyl, $C_1$–$C_4$-alkoxy, phenyl, benzyl, halogen, and OH, or $R^2$ and $R^3$ together with the nitrogen form a saturated or unsaturated 5- or 6-membered heterocyclic ring optionally containing nitrogen or oxygen as an additional heteroatom, the heterocyclic ring thereof linked via a single bond, a methylene-bridge, or spiro-connected to a saturated or unsaturated heterocyclic group containing one or two heteroatoms selected from oxygen and nitrogen, the heterocyclic group optionally mono- or di-substituted by a group selected from $CF_3$, $C_1$–$C_4$-alkyl, $C_1$–$C_4$-alkoxy, phenyl, benzyl, halogen, =O, and OH, or $R^2$ and $R^3$ together with the nitrogen form a saturated or unsaturated bi- or tricyclic heterocyclic ring-system optionally containing nitrogen or oxygen as an additional heteroatom, the heterocyclic ring-system being optionally substituted by a group selected from $CF_3$, $C_1$–$C_4$-alkyl, $C_1$–$C_4$-alkoxy, phenyl, benzyl, halogen, =O, and OH; and A is $C_1$–$C_6$-alkylene, $C_2$–$C_6$-alkenylene, or $C_2$–$C_6$-alkynylene, their pharmaceutically acceptable salts, their preparation, and their use for therapeutic purposes.

14 Claims, No Drawings

N,N'-DISUBSTITUTED BENZIMIDAZOLONE DERIVATIVES WITH AFFINITY AT THE SEROTONIN AND DOPAMINE RECEPTORS

RELATED APPLICATIONS

Benefit under 35 U.S.C. §119(e) of prior U.S. provisional application Serial No. 60/250,504, filed Dec. 1, 2000, is hereby claimed.

FIELD OF THE INVENTION

The present invention relates to novel pharmacologically active N,N'-disubstituted benzimidazolone derivatives and their addition salts which bind the serotonin or dopamine receptors, to their preparation and their use for therapeutic purposes. These compounds are able to discriminate the different serotonin and dopamine receptor subtypes like 5-$HT_{1A}$, 5-$HT_{2A}$, and $D_4$ at which they can act as agonists or antagonists. Owing to this pharmacological activity, the present compounds are useful in the treatment of anxiety disorders, affective disorders such as depression, psychosis and schizophrenia, eating disorders, sexual disorders, Parkinson, stroke and traumatic brain injury.

BACKGROUND OF THE INVENTION

Serotonin (5-HT) and dopamine (DA) recognize several well defined cell surface receptor subtypes. Among these, 5-$HT_{1A}$ and 5-$HT_{2A}$ having a high and a low affinity for 5-HT, respectively, and $D_4$ at which DA has high affinity, have been implicated in many Central Nervous System (CNS) disorders.

In the previous art, several classes of compounds able to interfere with the neurotransmission at 5-HT or DA receptor subtypes are known. Particularly, derivatives based on the core structure of the aryl piperazine and benzimidazolone have been described (e.g., GB 2023594, U.S. Pat. No. 3,472,854, U.S. Pat. No. 4,954,503, WO-9616949, WO-9501965, and WO-9833784), and targeted both to generic 5-HT or DA receptors and to a specific receptor subtype. In another patent (U.S. Pat. No. 5,576,318) are described compounds based both on the benzimidazolone and phenylpiperazine structures: in this latter case the described affinities are limited to 5-$HT_{1A}$ and 5-$HT_{2A}$ receptor subtypes.

DETAILED DESCRIPTION OF THE INVENTION

Now we describe, and this is the object of the present invention, new derivatives of a benzimidazolone core structure. The N-substituents are alkyl chains bearing additional hydrophilic functional groups whereas the N-substituents are alkyl or alkenyl spacers connecting the benzimidazolone scaffold to a large set of secondary amines bearing other diversity points. The compounds included in this invention possess an interesting affinity profile at the said serotonin and dopamine receptor subtypes: indeed some of them have a high and preferential affinity at a given site (e.g., 5-$HT_{1A}$, 5-$HT_{2A}$, or $D_4$) whereas some others have a mixed affinity at the said receptors. Moreover, a selected pool of compounds possesses an agonistic activity at the 5-$HT_{1A}$ receptor coupled with an antagonistic activity at the 5-$HT_{2A}$ receptor. Owing to their peculiar profile, the present compounds may play a role in the regulation of neurotransmission at the serotonin and/or the dopamine sites and thus may be of value in the treatment of those diseases where an altered functioning of neurosignal transmission is present. Examples of these disorders include anxiety, depression, schizophrenia, Parkinson, sleep, sexual and eating disorders, stroke and brain injury. Particularly the compounds included in the present invention can be of value in the treatment of depression according to the mounting evidence that 5-$HT_{1A}$ full agonists or high efficiency partial agonists are required for a robust antidepressant effect. In fact, electrophysiology studies suggest that repeated administration of a variety of antidepressant treatments facilitate 5-$HT_{1A}$ neurotransmission in the hippocampus, possibly through either an increased sensitivity of post-synaptic 5-$HT_{1A}$ receptors or a decreased sensitivity of 5-$HT_{1A}$ autoreceptors. Furthermore, there is some evidence from controlled clinical trials to support this suggestion. In addition the compound's ability to block the 5-$HT_{2A}$ receptor is also of value: indeed, the stimulation of 5-$HT_{1A}$ and 5-$HT_{2A}$ receptors lead to opposite electrical events, inhibitory and excitatory, respectively. Thus only a concurrent activation of 5-$HT_{1A}$ coupled with antagonism at 5-$HT_{2A}$ receptors may completely and rapidly inhibit 5-HT post-synaptic cells, an important physiological event for antidepressant effects.

The present invention pertains to compounds of general formula (I)

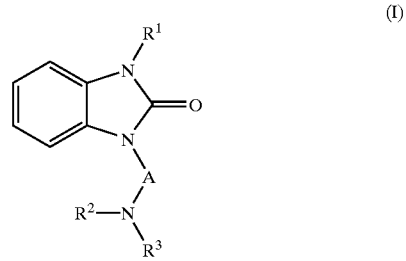

(I)

wherein:
  $R^1$ denotes $C_1$–$C_6$-alkyl, preferably $C_1$–$C_4$-alkyl, being substituted by a group selected from OH, $C_1$–$C_6$-alkoxy, —OCONH$C_1$–$C_6$-alkyl, —OCONH$C_1$–$C_6$-alkyl, —NHSO$_2C_1$–$C_6$-alkyl, and —NHCO$C_1$–$C_6$-alkyl, or
  $R^1$ denotes $C_1$–$C_6$-alkyl, preferably $C_1$–$C_4$-alkyl, being substituted by a saturated or unsaturated 5- or 6-membered heterocycle containing one or two heteroatoms selected from the group consisting of nitrogen and oxygen, said heterocycle being optionally substituted by a group selected from $C_1$–$C_4$-alkyl, halogen, and benzyl;
  $R^2$ and $R^3$ together with the nitrogen form a saturated or unsaturated 5- or 6-membered heterocyclic ring which may contain nitrogen or oxygen as an additional heteroatom, whilst the heterocyclic ring is substituted by a group selected from phenyl, benzyl, and diphenylmethyl, said group being optionally mono- or di-substituted by one or two groups selected from $CF_3$, $C_1$–$C_4$-alkyl, $C_1$–$C_4$-alkoxy, phenyl, benzyl, halogen, and OH, or
  $R^2$ and $R^3$ together with the nitrogen form a saturated or unsaturated 5- or 6-membered heterocyclic ring which may contain nitrogen or oxygen as an additional heteroatom, said heterocyclic ring being linked via a single bond, a methylene-bridge or spiro-connected to another saturated or unsaturated heterocyclic group containing one or two heteroatoms selected from oxygen and nitrogen, said heterocyclic group being optionally mono- or di-substituted by a group selected from CF$_3$, C$_1$–C$_4$-alkyl, C$_1$–C$_4$-alkoxy, phenyl, benzyl, halogen, =O, and OH, or R$^2$ and R$^3$ together with the nitrogen form a saturated or unsaturated bi- or tricyclic heterocyclic ring-system which may contain nitrogen or oxygen as an additional heteroatom, said heterocyclic ring-system being optionally substituted by a group selected from CF$_3$, C$_1$–C$_4$-alkyl, C$_1$–C$_4$-alkoxy, phenyl, benzyl, halogen, =O, and OH;

A denotes C$_1$–C$_6$-alkylene, preferably C$_1$–C$_4$-alkylene, C$_2$–C$_6$-alkenylene, preferably C$_2$–C$_4$-alkenylene, or C$_2$–C$_6$-alkynylene, preferably C$_2$–C$_4$-alkynylene, or a pharmaceutically acceptable salt thereof.

Preferred compounds are those of formula (I), wherein:

R$^1$ denotes C$_1$–C$_4$-alkyl, preferably C$_2$–C$_3$-alkyl, being substituted by a group selected from OH, C$_1$–C$_4$-alkoxy, —OCONHC$_1$–C$_4$-alkyl, —OCONHC$_1$–C$_4$-alkyl, —NHSO$_2$C$_1$–C$_4$-alkyl, and —NHCOC$_1$–C$_4$-alkyl, or R$^1$ denotes C$_1$–C$_4$-alkyl, preferably C$_2$–C$_3$-alkyl, being substituted by a saturated or unsaturated 6-membered heterocycle containing one or two heteroatoms selected from the group consisting of nitrogen and oxygen;

R$^2$ and R$^3$ together with the nitrogen form a saturated or unsaturated 5- or 6-membered heterocyclic ring which may contain nitrogen as an additional heteroatom, whilst the heterocyclic ring is substituted by a group selected from phenyl, benzyl, diphenylmethyl, pyridinyl, pyrimidinyl, benzimidazolonyl, and 3,4-methylenedioxibenzyl, said group being optionally mono- or di-substituted by a group selected from CF$_3$, C$_1$–C$_4$-alkyl, C$_1$–C$_4$-alkoxy, halogen, and OH;

A denotes C$_1$–C$_4$-alkylene or C$_2$–C$_4$-alkenylene, or a pharmaceutically acceptable salt thereof.

Also preferred compounds are those of formula (I), wherein:

R$^1$ denotes ethyl, being substituted by a group selected from OH, OCH$_3$, OCH$_2$CH$_3$, —OCONHCH$_3$, —OCONHCH$_2$CH$_3$, —NHSO$_2$CH$_3$, —NHSO$_2$CH$_2$CH$_3$, —NHCOCH$_3$, —NHCOCH$_2$CH$_3$, morpholinyl, piperazinyl, and piperidinyl R$^2$ and R$^3$ together with the nitrogen form a 6-membered saturated or unsaturated heterocyclic ring which may contain nitrogen as an additional heteroatom, whilst the heterocyclic ring is substituted by a group selected from phenyl, pyridinyl, pyrimidinyl, benzimidizalonyl, and substituted phenyl being mono- or di-substituted by a group selected from CF$_3$, CH$_3$, OCH$_3$, F, and Cl;

A denotes C$_1$–C$_4$-alkylene or C$_2$–C$_4$-alkenylene, or a pharmaceutically acceptable salt thereof.

Also of interest are compounds of formula (I), wherein:

R$^1$ denotes ethyl, being substituted by a group selected from OH, OCH$_3$, —OCONHCH$_2$CH$_3$, —NHSO$_2$CH$_3$, —NHCOCH$_3$, morpholinyl, and piperidinyl;

R$^2$ and R$^3$ together with the nitrogen form a 6-membered saturated or unsaturated heterocyclic ring which may contain nitrogen as an additional heteroatom, whilst the heterocyclic ring is substituted by a group selected from pyridinyl, phenyl, and substituted phenyl being mono- or di-substituted by a group selected from CF$_3$, CH$_3$, OCH$_3$, F, and Cl;

A denotes ethylene, propylene, butylene, or butenylene, or a pharmaceutically acceptable salt thereof.

Of particular interest are compounds of formula (I), wherein:

R$^1$ denotes ethyl, being substituted by a group selected from OH, OCH$_3$, —OCONHCH$_2$CH$_3$, —NHSO$_2$CH$_3$, —NHCOCH$_3$, morpholinyl, and piperidinyl;

R$^2$ and R$^3$ together with the nitrogen form a ring selected from the group consisting of piperazine, piperidine, and tetrahydropyridine, which is substituted by a group selected from pyridinyl, phenyl, and substituted phenyl being mono- or di-substituted by a group selected from CF$_3$, CH$_3$, and Cl;

A denotes ethylene, butylene, or butenylene, or a pharmaceutically acceptable salt thereof.

Furthermore preferred are compounds of formula (I), wherein:

R$^1$ denotes ethyl, being substituted by a group selected from OH, OCH$_3$, —OCONHCH$_2$CH$_3$, and —NHSO$_2$CH$_3$;

R$^2$ and R$^3$ together with the nitrogen form a piperazine ring, being substituted by a group selected from trifluoromethylphenyl, methylphenyl, dimethylphenyl, and chlorophenyl; and A denotes ethylene, butylene, or butenylene, or a pharmaceutically acceptable salt thereof.

The most preferred compounds according to the invention are:

(a) 1-(2-methoxyethyl)-3-(4-{4-[3-(trifluoromethyl)phenyl]-1-piperazinyl}butyl)-1,3-dihydro-2H-benzimidazol-2-one;

(b) 1-{4-[4-(2,3-dimethylphenyl)-1-piperazinyl]butyl}-3-(2-hydroxyethyl)-1,3-dihydro-2H-benzimidazol-2-one;

(c) 2-[2-oxo-3-(4-{4-[3-(trifluoromethyl)phenyl]-1-piperazinyl}butyl)-2,3-dihydro-1H-benzimidazol-1-yl]ethyl-ethylcarbamate;

(d) 1-(2-methoxyethyl)-3-(2-{4-[3-(trifluoromethyl)phenyl]-1-piperazinyl}ethyl)-1,3-dihydro-2H-benzimidazol-2-one;

(e) 1-{2-[4-(2,3-dimethylphenyl)-1-piperazinyl]ethyl}-3-(2-methoxyethyl)-1,3-dihydro-2H-benzimidazol-2-one;

(f) 1-{2-[4-(3-chlorophenyl)-1-piperazinyl]ethyl}-3-(2-hydroxyethyl)-1,3-dihyddro-2H-benzimidazol-2-one;

(g) 2-[2-oxo-3-(2-{4-[3-(trifluoromethyl)phenyl]-1-piperazinyl}ethyl)-2,3-dihydro-1H-benzimidazol-1-yl]ethyl-ethylcarbamate;

(h) 2-(3-{2-[4-(2,3-dimethylphenyl)-1-piperazinyl]ethyl}-2-oxo-2,3-dihydro-1H-benzimidazol-1-yl)ethyl-ethylcarbamate;

(i) N-[2-(3-{2-[4-(2,3-dimethylphenyl)-1-piperazinyl]ethyl}-2-oxo-2,3-dihydro-1H-benzimidazol-1-yl)ethyl]methanesulfonamide;

(j) N-[2-(3-{(2Z)-4-[4-(3-methylphenyl)-1-piperazinyl]-2-butenyl}-2-oxo-2,3-dihydro-1H-benzimidazol-1-yl)ethyl]methanesulfonamide; and (k) N-[2-(3-{(2E)-4-[4-(3-chlorophenyl)-1-piperazinyl]-2-butenyl}-2-oxo-2,3-dihydro-1H-benzimidazol-1-yl)ethyl]methanesulfonamide.

If required, the compounds of general formula (I) may be converted into the salts thereof, particularly, for pharmaceutical use, into the pharmaceutically acceptable salts thereof with an inorganic or organic acid. Suitable acids for this purpose include hydrochloric acid, hydrobromic acid, sulfuric acid, phosphoric acid, methanesulfonic acid, acetic acid, fumaric acid, succinic acid, lactic acid, citric acid, tartaric acid, or maleic acid. Moreover, mixtures of these acids may be used.

The alkyl groups meant here (including those which are components of other groups) are branched and unbranched alkyl groups having 1 to 6 carbon atoms, preferably 1 to 4 carbon atoms, such as: methyl, ethyl, n-propyl, isopropyl, butyl, isobutyl, sec-butyl, tert-butyl, pentyl, isopentyl, and hexyl.

The alkylene groups meant here are branched and unbranched alkyl-bridges having 1 to 6 carbon atoms, preferably 1 to 4 carbon atoms, such as: methylene, ethylene, n-propylene, isopropylene, butylene, isobutylene, sec-butylene, tert-butylene, pentylene, isopentylene, and hexylene.

Alkenyl groups (including those which are components of other groups) are the branched and unbranched alkenyl groups with 2 to 6 carbon atoms, preferably 2 to 4 carbon atoms, provided that they have at least one double bond, e.g., the alkyl groups mentioned above provided that they have at least one double bond, such as for example vinyl (provided that no unstable enamines or enolethers are formed), propenyl, isopropenyl, butenyl, pentenyl, and hexenyl.

Alkenylene groups are the branched and unbranched alkenyl-bridges with 2 to 6 carbon atoms, preferably 2 to 4 carbon atoms, provided that they have at least one double bond, e.g., the alkylene groups mentioned above provided that they have at least one double bond, such as for example vinylene (provided that no unstable enamines or enolethers are formed), propenylene, isopropenylene, butenylene, pentenylene, and hexenylene.

If not otherwise specified the alkenyl-and alkenylene-groups mentioned above are to be understood as embracing optionally existing stereoisomers. Accordingly, for instance the definition 2-butenyl is to be understood as embracing 2-(Z)-butenyl and 2-(E)-butenyl, etc.

The term alkynyl groups (including those which are components of other groups) refers to alkynyl groups having 2 to 6, preferably 2 to 4 carbon atoms, provided that they have at least one triple bond, e.g., ethynyl, propargyl, butynyl, pentynyl, and hexynyl.

Examples of N-linked 5- or 6-membered heterocyclic rings of general formula $NR^2R^3$ are as follows: pyrrole, pyrroline, pyrrolidine, piperidine, piperazine, morpholine, imidazole, imidazoline, imidazolidine, pyrazole, pyrazoline, and pyrazolidine, preferably morpholine, piperazine, and piperidine.

Examples of saturated or unsaturated bi- or tricyclic heterocyclic ring-system of formula $NR^2R^3$ which may contain nitrogen or oxygen as an additional heteroatom, are as follows: indole, tetrahydroindole, benzimidazole, benzoxazole, 1,2-dihydrochinoline, 1,2-dihydroisochinoline, β-carboline, 9H-1,2,3,4-tetrahydropyridoindole, and 9,10-dihydroacridine.

Halogen means fluorine, chlorine, bromine, or iodine, preferably chlorine or bromine.

"=O" means an oxygen atom linked by a double bond.

The compounds of general formula (I) may be conveniently prepared by a variety of synthetic processes analogous to those known in the art using conventional methods. For example, these compounds may be prepared by alkylating the suitable secondary amine (III) with the proper benzimidazolone (II) bearing in the alkyl or alkenyl side chain suitable leaving group X such as halogen, methanesulfonate, or 4-methylbenzenesulfonate (Scheme 1).

Scheme 1

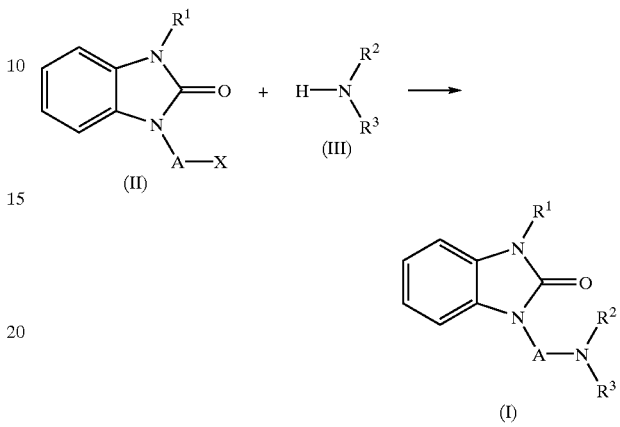

Scheme 1:

The reaction conditions for the conventional synthesis of compounds of formula (I) according to Scheme 1 are disclosed in EP 526 434 A1. Said reference additionally describes the possible synthetic pathways for the preparation of starting compounds (II). According to a second option, the reaction sequence according to Scheme 1 can not only be conducted via the conventional synthetic methods outlined in EP 526 434 A1 but, in the alternative, via combinatorial chemistry. For this approach a set of N-alkyl-N'-halo alkyl/alkenyl benzimidazolones of formula (II) (hereinafter identified as Building Blocks or BB; see hereto Table 1) was prepared via the traditional methods described in EP 526 434 A1 and then combinatorial reacted with the suitable secondary amines of formula (III) (Table 2). The process was carried out in a special apparatus consisting of a lower vial (reacting chamber) and an upper vial (condenser). Each compound was reacted with each amine in DMF under stirring at a temperature between 40° C. and 100° C., preferably at 60° C., for 6 to 8 hours in the presence of $Na_2CO_3$. The excess amine was then scavenged at room temperature by introducing a polystyrene isocyanatemethyl resin of formula (IV) able to catch the excess amine as an urea of formula (V) immobilized on the solid support (Scheme 2).

Scheme 2

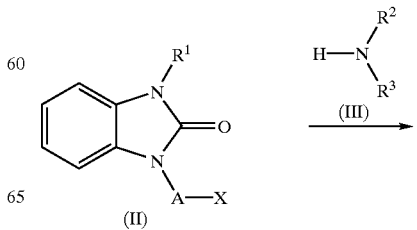

-continued

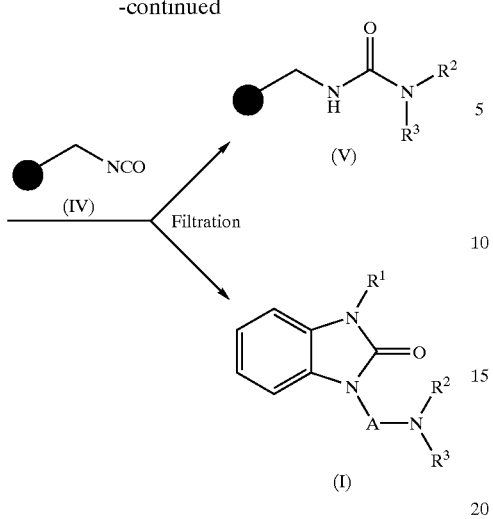

Scheme 2:

The upper part of the reaction apparatus is substituted with another vial containing a frit inside and a connection to the vacuum. Filtration after turning over the apparatus and evaporation to dryness afforded the desired compounds of formula (I) in excellent yield and good purity. The parallel application of the aforementioned process to all of the compounds of formula (II) as shown in Table 1 and all of the selected amines (III) as shown in Table 2 allows the efficient synthesis of all of the compounds (I) according to the present invention.

TABLE 1

Building Blocks (BB) of Formula (II) Subjected to the Process of Scheme 2

(II)

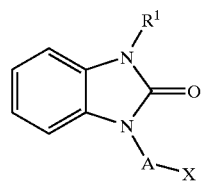

| Building Block No. | Structure |
|---|---|
| BB01 | 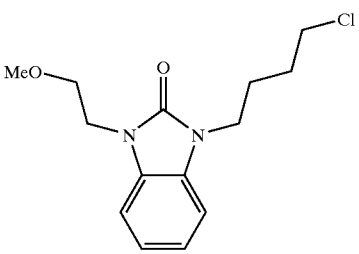 |
| BB02 | 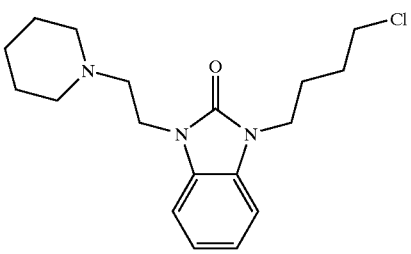 |

TABLE 1-continued

Building Blocks (BB) of Formula (II) Subjected to the Process of Scheme 2

(II)

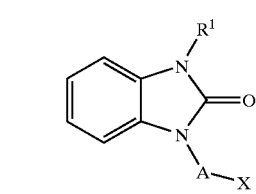

| Building Block No. | Structure |
|---|---|
| BB03 | 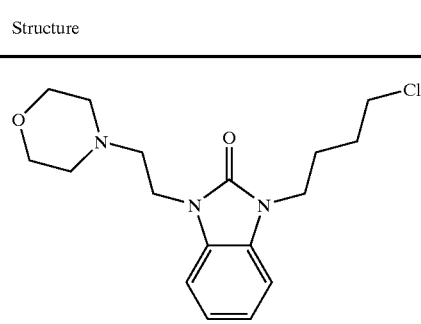 |
| BB04 | 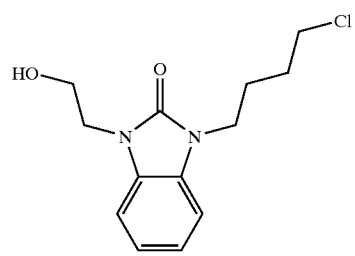 |
| BB05 | 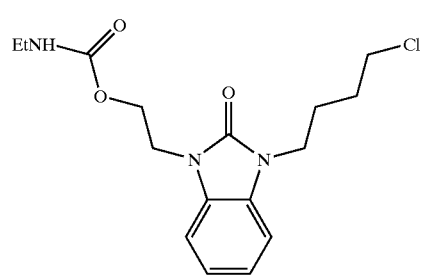 |
| BB06 | 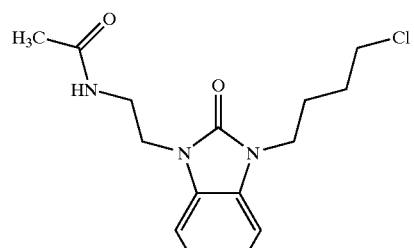 |

TABLE 1-continued
Building Blocks (BB) of Formula (II) Subjected to the Process of Scheme 2
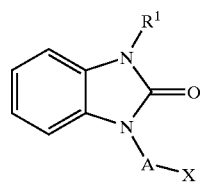
(II)
| Building Block No. | Structure |
|---|---|
| BB07 | 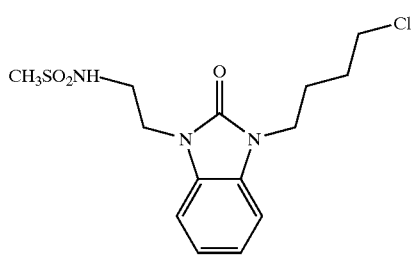 |
| BB08 | 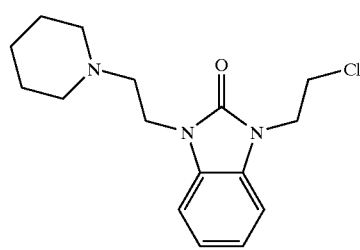 |
| BB09 | 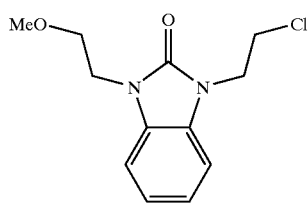 |
| BB10 | 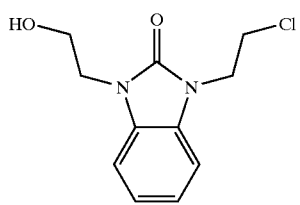 |
| BB11 | 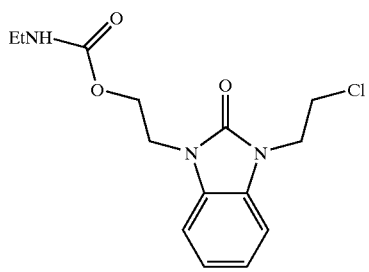 |
TABLE 1-continued
Building Blocks (BB) of Formula (II) Subjected to the Process of Scheme 2
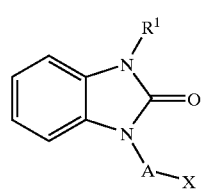
(II)
| Building Block No. | Structure |
|---|---|
| BB12 | 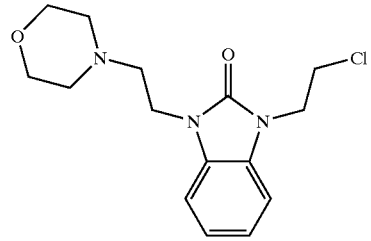 |
| BB13 | 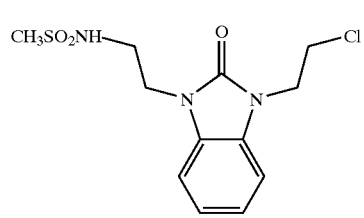 |
| BB14 | 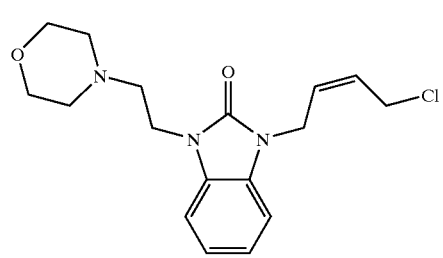 |
| BB15 | 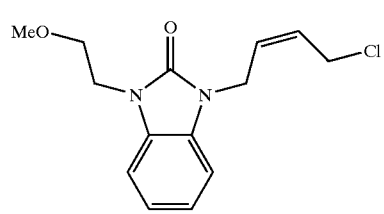 |
| BB16 | 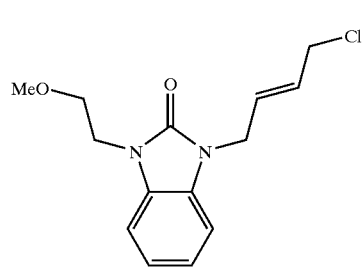 |

TABLE 1-continued

Building Blocks (BB) of Formula (II) Subjected to the Process of Scheme 2

(II)

| Building Block No. | Structure |
|---|---|
| BB17 | (piperidine-ethyl benzimidazolone with cis-4-chlorobut-2-enyl) |
| BB18 | (piperidine-ethyl benzimidazolone with trans-4-chlorobut-2-enyl) |
| BB19 | (morpholine-ethyl benzimidazolone with trans-4-chlorobut-2-enyl) |
| BB20 | (HO-ethyl benzimidazolone with cis-4-chlorobut-2-enyl) |
| BB21 | (HO-ethyl benzimidazolone with trans-4-chlorobut-2-enyl) |
| BB22 | (EtNH-C(O)O-ethyl benzimidazolone with cis-4-chlorobut-2-enyl) |
| BB23 | (EtNH-C(O)O-ethyl benzimidazolone with trans-4-chlorobut-2-enyl) |
| BB24 | (H$_3$C-C(O)NH-ethyl benzimidazolone with 2-chloroethyl) |
| BB25 | (H$_3$C-C(O)NH-ethyl benzimidazolone with cis-4-chlorobut-2-enyl) |

TABLE 1-continued

Building Blocks (BB) of Formula (II) Subjected to the Process of Scheme 2

(II)

| Building Block No. | Structure |
|---|---|
| BB26 | H₃C-C(O)-NH-CH₂CH₂-N(benzimidazolone)N-CH₂-CH=CH-CH₂-Cl |
| BB27 | CH₃SO₂NH-CH₂CH₂-N(benzimidazolone)N-CH₂-CH=CH-CH₂-Cl (cis) |
| BB28 | CH₃SO₂NH-CH₂CH₂-N(benzimidazolone)N-CH₂-CH=CH-CH₂-Cl (trans) |

TABLE 2

Amines (AM) of Formula (III) Subjected to the Process of Scheme 2

(III)

| Amine No. | Structure |
|---|---|
| AM01 | 1-phenylpiperazine |
| AM02 | 1-[(4-chlorophenyl)(phenyl)methyl]piperazine |
| AM03 | 1-benzylpiperazine |
| AM04 | 1-(2-pyridyl)piperazine |
| AM05 | 1-(3-chlorophenyl)piperazine |
| AM06 | 1-(2-pyrimidyl)piperazine |
| AM07 | 2,3,4,5-tetrahydro-1H-pyrido[3,4-b]indole |
| AM08 | 1-(3,5-dichloropyridin-4-yl)piperazine |
| AM09 | 1-[3-(trifluoromethyl)phenyl]piperazine |
| AM10 | 4-phenyl-1,2,3,6-tetrahydropyridine |

TABLE 2-continued

Amines (AM) of Formula (III) Subjected to the Process of Scheme 2

(III)

$$H-N\begin{matrix}R^2\\ \\R^3\end{matrix}$$

| Amine No. | Structure |
|---|---|
| AM11 | 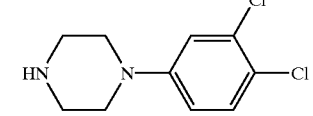 |
| AM12 | 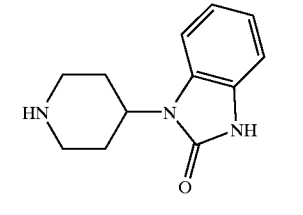 |
| AM13 | 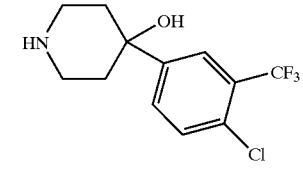 |
| AM14 | 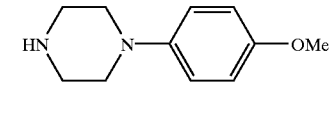 |
| AM15 | 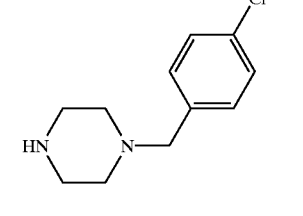 |
| AM16 | 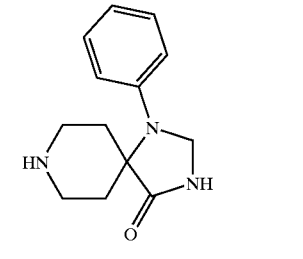 |
| AM17 | 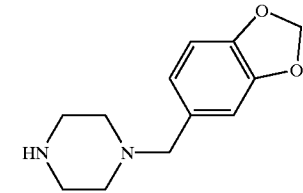 |
| AM18 | 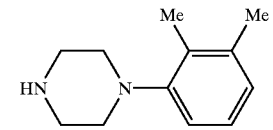 |
| AM19 | 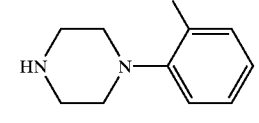 |
| AM20 | 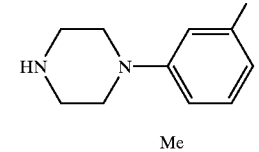 |
| AM21 | 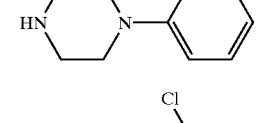 |
| AM22 | 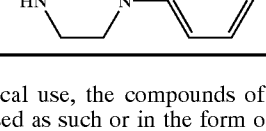 |

For pharmaceutical use, the compounds of general formula (I) may be used as such or in the form of physiologically acceptable acid addition salts. The term "physiologically acceptable acid addition salts" includes the salts resulting from both organic and inorganic acids such as maleic, citric tartaric, methanesulfonic, acetic, benzoic, succinic, gluconic, isethionic, glycinic, lactic, malic, mucoic, glutammic, sulfamic, and ascorbic acids; inorganic acids include hydrochloric, hydrobromic, nitric, sulfuric, or phosphoric acid.

According to a further feature of the present invention, there are provided pharmaceutical compositions comprising as an active ingredient at least one compound of formula (I), as before defined, or a physiologically acceptable addition salt thereof in addition to one or more pharmaceutical carrier, diluents or excipients. For pharmaceutical administration, the compounds of general formula (I) and their physiologically acceptable acid addition salts may be incorporated into the conventional pharmaceutical preparation in solid, liquid, or spray form. The composition may, for example, be presented in a form suitable for oral, rectal, or parenteral administration or for nasal inhalation: preferred forms include, for example, capsules, tablets, coated tables, ampoules, suppositories, and nasal spray. The active ingredient may be incorporated in excipients or carriers conventionally used in pharmaceutical compositions such as, for example, talc, arabic gum, lactose, gelatine, magnesium stearate, corn starch, aqueous or nonaqueous vehicles, polyvinyl pyrrolidone, semisynthetic glycerides of fatty acids, benzalcon chloride, sodium phosphate, EDTA, or polysorbate 80.

In case it is desired to further increase the solubility of the compounds of general formula (I) or of their physiologically acceptable salts, surfactants or nonionic surfactants such as PEG 400, cyclodextrin, metastable polymorphs, or inert adsorbents such as bentonite, may be incorporated. Furthermore, some techniques may be employed by preparing, for example, eutectic mixtures and/or solid dispersion by using mannitol, sorbitol, saccharose, or succinic acid or physically-modified forms by using hydrosoluble polymers, PVP, or PEG 4000–20,000. The compositions are advantageously formulated in dosage units, each dosage unit being adapted to supply a single dose of the active ingredient. Each dosage unit may conveniently contain from 0.01 mg to 100 mg, preferably from 0.1 to 50 mg.

However, it could be necessary to depart from the cited amounts, depending on the body weight or on the administration route, on the individual response to the medicament, on the type of formulation and on the time, or time range, in which the administration is carried out. Therefore, it can be sufficient, in some cases, to use a lower amount then the cited minimum amount, whereas in other cases the higher range could be exceeded. When administering higher amounts, it would be advisable to subdivide them in repeated administrations during the day. Moreover, the compounds of general formula (I) or the acid addition salts thereof can also be combined with other, different active substances.

The following examples illustrate the present invention, without limiting the scope thereof.

EXAMPLES OF PHARMACEUTICAL FORMULATIONS

| A. Tablets Containing 100 mg of Active Substance | |
| --- | --- |
| Component | Amount per tablet (mg) |
| active substance | 100 |
| lactose | 140 |
| maize starch | 240 |
| polyvinylpyrrolidone | 15 |
| magnesium stearate | 5 |
| TOTAL | 500 |

The finely ground active substance, lactose, and part of maize starch are mixed. The mixture is sieved, wetted with a solution of polyvinylpyrrolidone in water, kneaded, finely granulated, and dried. The granulate, the remaining maize starch, and magnesium stearate are sieved and mixed together. The mixture is compressed to tablets of suitable form and size.

| B. Tablets Containing 80 mg of Active Substance | |
| --- | --- |
| Component | Amount per tablet (mg) |
| active substance | 80 |
| lactose | 55 |
| maize starch | 190 |
| polyvinylpyrrolidone | 15 |
| sodium carboxymethyl starch | 23 |
| magnesium stearate | 2 |
| TOTAL | 400 |

The finely ground active substance, part of the maize starch, lactose, microcrystalline cellulose and polyvinylpyrrolidone are mixed. The mixture is sieved and worked up with the remaining maize starch and water, to obtain a granulate, which is dried and sieved. This is added to sodium carboxymethyl starch and magnesium stearate and mixed, and the mixture is then compressed to tablets of suitable size.

| C. Solutions for Vials | |
| --- | --- |
| Component | Amount |
| active substance | 50 mg |
| sodium chloride | 50 mg |
| water for injection | 5 ml |

The active substance is dissolved in water, optionally at pH of 5.5 to 6.5, and treated with sodium chloride as an osmolality agent. The resulting solution is filtered apyrogenically, and the filtrate is placed in vials under aseptic conditions, then the vials are sterilized and flame sealed. The vials contain 5 mg, 25 mg, and 50 mg of active substance.

EXPERIMENTAL

The following examples illustrate the preparation of all the new compounds included in the present invention. It should be understood that the invention is not limited to the given examples of chemical methods and processes for the preparation of the substances, as other conventional methods well known to those skilled in the art, are suitable too. In the following descriptions, each of the 28 Building Blocks prepared is identified by its relevant Tag.

A. Preparation of the Building Blocks (BB) of Formula (II)

Description 1

1-[2-(1-Piperidinyl)ethyl]-1,3-dihydro-2H-benzimidazol-2-one

A solution of 1-isopropenyl-1,3-dihydro-2H-benzimidazol-2-one (35 g, 0.2 moles) in DMF (250 ml) was added dropwise to a suspension of 80% sodium hydride (6 g, 0.2 moles) in DMF (50 ml). The reaction mixture was first heated at 45° C. for 30 minutes, allowed to cool at room temperature, and an additional amount of 80% sodium hydride (7.2 g, 0.24 moles) was added. Then 1-(2-chloroethyl)piperidine hydrochloride (44.16 g, 0.24 moles) was added portionwise and the reaction mixture was heated at 80° C.–90° C. for 3 hours. The mixture was then cooled at room temperature, adjusted to pH 3 with 37% aqueous HCl, and heated to 80° C. for additional 2 hours. The reaction mixture was poured into water and washed with ethyl acetate. The aqueous phase was adjusted to pH 8–9 with a saturated sodium carbonate solution and extracted into ethyl acetate. The organic layer was taken to dryness to give an ivory solid which after crystallization from isopropyl ether afforded 22.9 g of the title compound. M.p. 123° C.–125° C.

According to the above described procedure, the following compound was prepared from the suitable intermediates:
1-[2-(4-Morpholinyl)ethyl]-1,3-dihydro-2H-benzimidazol-2-one 11.7 g; m.p. 122° C.–126° C.

Description 2
1-(2-Methoxyethyl)-1,3-dihydro-2H-benzimidazol-2-one

Phenyl-2-oxo-2,3-dihydro-1H-benzimidazole-1-carboxylate (80 g, 0.315 moles) was added to a suspension of 80% sodium hydride (11.3 g, 0.378 moles) in DMF (500 ml) and heated at 35° C. for 1 hour. To the cooled solution, 2-chloroethylmethylether (43 ml, 0.472 moles) was added and the reaction mixture was heated at 100° C. for 4 hours. The reaction mixture was poured into water and extracted with ethyl acetate. The combined extracts were taken to dryness to give 52 g of the protected intermediate. This was suspended in methanol (500 ml), a solution of $K_2CO_3$ (44 g) in water (230 ml) was added, and the mixture and stirred for 2 hours at room temperature. After evaporation, the reaction mixture was acidified and extracted into ethyl acetate. The organic layer was taken to dryness and from the crude oily residue, after crystallization with isopropyl ether, 21 g of the title compound was obtained as a white solid. M.p. 88° C.

Description 3
1-[2-(Tetrahydro-2H-pyran-2-yloxy)ethyl]-1,3-dihydro-2H-benzimidazol-2-one (a) Phenyl-2-oxo-2,3-dihydro-1H-benzimidazole-1-carboxylate (50 g, 0.197 moles) was added to a suspension of 80% sodium hydride (7 g, 0.236 moles) in DMF (400 ml) and stirred for 1 hour at room temperature, then 2-(2-chloroethoxy)tetrahydro-2H-pyran (34.8 ml, 0.236 moles) was added and the reaction mixture was heated at 100° C. for 7 hours. The reaction mixture was then poured into water and extracted into ethyl acetate. The organic layer was taken to dryness to give an oily residue.

(b) This residue (83 g) was dissolved in methanol, a solution of KOH (26 g in 260 ml water) was added and stirred for 2 hours at room temperature. The methanol was evaporated and the residue was extracted into ethyl acetate. The organic layer was washed with an aqueous 5% HCl solution, dried, and taken to dryness. The oily residue was crystallized from diisopropyl ether to give 26 g of the title compound. M.p. 115° C.

Description 4
1-(2-Aminoethyl)-1,3-dihydro-2H-benzimidazol-2-one Hydrochloride (a) A suspension of phenyl-2-oxo-2,3-dihydro-1H-benzimidazole-1-carboxylate (10 g, 39 mmoles) and 80% sodium hydride (1.3 g, 43 mmoles) in DMF (100 ml) was stirred at room temperature for 30 minutes. N-(2-bromoethyl)phthalimide (10 g, 39 mmoles) was added and the mixture heated at 100° C. for 12 hours. The reaction mixture was then poured into 600 ml of water and stirred for 4 hours at room temperature. The precipitated phthaloyl derivative was filtered off (white solid; 6.5 g).

(b) This intermediate was suspended in methanol (70 ml), a 10% aqueous $K_2CO_3$ solution was added and the reaction mixture stirred overnight at room temperature. The methanol was evaporated, the residue was extracted with dichloromethane, and the aqueous solution was acidified with 10% aqueous HCl to give the corresponding 2-carboxybenzamido derivative which was filtered off (5 g).

(c) To the crude intermediate was added 32 ml of a 15% aqueous HCl solution and the resulting suspension was heated at 90° C. for 3 hours. After cooling, the solid was filtered off and the acidic solution was taken to dryness to give 1.5 g of the hydrochloride of the title compound as a pinkish solid. M.p. >280° C.

Description 5
N-[2-(2-oxo-2,3-Dihydro-1H-benzimidazol-1-yl)ethyl]-acetamide

To a cooled solution of NaOH (0.41 g, 10 mmoles) in water (5 ml) were simultaneously added 1-(2-aminoethyl)-1,3-dihydro-2H-benzimidazol-2-one hydrochloride (0.7 g, 3.3 mmoles) and a solution of acetic anhydride (0.37 ml, 3.9 mmoles) in dioxane (10 ml). The reaction mixture was stirred for 2 hours at room temperature and then taken to dryness. The residue was dissolved in water, adjusted to pH 4 with 10% aqueous HCl, and extracted with $CHCl_3$. The organic layer was taken to dryness and from the crude residue 0.35 g of the title compound was obtained after crystallization from diethyl ether. M.p. 153° C.

Description 6
N-[2-(2-oxo-2,3-Dihydro-1H-benzimidazol-1-yl)ethyl] methanesulfonamide To a solution of 1-(2-aminoethyl)-1,3-dihydro-2H-benzimidazol-2-one hydrochloride (2.8 g, 13 mmoles) in THF (30 ml) and triethyl amine (5.5 ml, 39 mmoles) was added methanesulfonyl chloride (1.12 ml, 14 mmoles) and the reaction mixture was stirred for 2 hours at room temperature. The organic solvent was evaporated and the residue was partitioned into water and ethyl acetate. The organic layer was washed with saturated aqueous $Na_2CO_3$ solution and taken to dryness. The crude residue was purified by flash chromatography ($CH_2Cl_2$-methanol 96-4) to give 0.5 g of the title compound as a white solid. M.p. 162–170° C.

Description 7
1-(2-Chloroethyl)-3-[2-(tetrahydro-2H-pyran-2-yloxy) ethyl]-1,3-dihydro-2H-benzimidazol-2-one Into a stirred solution of 1-[2-(tetrahydro-2H-pyran-2-yloxy)ethyl]-1,3-dihydro-2H-benzimidazol-2-one (6.5 g, 25 mmoles) in DMF (40 ml) 80% sodium hydride (0.9 g, 30 mmoles) was added. After 30 minutes of stirring and heating to 35° C., 1-bromo-2-chloroethane (6.2 g, 48 mmoles) was added, the reaction temperature was increased to 90° C. and kept for 6 hours then cooled at room temperature. The reaction mixture was poured into water, extracted with diethyl ether, and the organic layer was taken to dryness. The residue was purified by flash chromatography (cyclohexane-ethyl acetate 50-50) to give 2.8 g of the title compound as a thick oil which was used without any further purification.

According to the above described procedure, the following compounds were prepared from the suitable intermediates:
1-(4-Chlorobutyl)-3-[2-(tetrahydro-2H-pyran-2-yloxy) ethyl]-1,3-dihydro-2H-benzimidazol-2-one The compound was purified by flash chromatography (cyclohexane-ethyl acetate 50-50). Thick oil.

[BB09]: 1-(2-Chloroethyl)-3-(2-methoxyethyl)-1,3-dihydro-2H-benzimidazol-2-one

White solid. M.p. 55° C., from diisopropyl ether.

[BB01]: 1-(4-Chlorobutyl)-3-(2-methoxyethyl)-1,3-dihydro-2H-benzimidazol-2-one

The compound was purified by flash chromatography (cyclohexane-ethyl acetate 50-50). Thick oil.

[BB15]: 1-[(2Z)4-Chloro-2butenyl)]-3-(2-methoxyethyl)-1,3-dihydro-2H-benzimidazol-2-one The compound was purified by flash chromatography (cyclohexane-ethyl acetate 70-30). Thick oil.

[BB24]: N-{2-[3-(2-Chloroethyl)-2-oxo-2,3-dihydro-1H-benzimidazol-1-yl]ethyl}-acetamide White solid. M.p. 140° C.–142° C., from acetone.

[BB06]: N-{2-[3-(4-Chlorobutyl)-2-oxo-2,3-dihydro-1H-benzimidazol-1-yl]ethyl}-acetamide Ivory solid. M.p. 100° C., from diethyl ether.

Description 8

1-[(2Z)-4-Chloro-2-butenyl]-3-[2-(tetrahydro-2H-pyran-2-yloxy)ethyl]-1,3-dihydro-2H-benzimidazol-2-one To a solution of 1-[2-(tetrahydro-2H-pyran-2yloxy)ethyl]-1,3-dihydro-2H-benzimidazol-2-one (12 g, 46 mmoles) in DMF (120 ml) was added 80% sodium hydride (1.7 g, 55 mmoles) and the mixture was stirred at room temperature for 1 hour. Cis-1,4-dichloro-2-butene (5.8 ml, 55 mmoles) was added dropwise and the reaction mixture was stirred for 3 hours at room temperature. The reaction mixture was poured into water and extracted with ethyl acetate. The organic layer was taken to dryness and the residue was purified by flash chromatography (cyclohexane-ethyl acetate 70-30) to give 2.8 g of the title compound as a thick oil which was used without any further purification.

According to the above described procedure, the following compounds were prepared from the suitable intermediates:

1-[(2E)4-Chloro-2-butenyl)]-3-[2-(tetrahydro-2H-pyran-2-yloxy)ethyl]-1,3-dihydro-2H-benzimidazol-2-one The compound was purified by flash chromatography (cyclohexane-ethyl acetate 70-30). Waxy solid.

[BB 16]: 1-[(2E)-4-Chloro-2-butenyl)]-3-(2-methoxyethyl)-1,3-dihydro-2H-benzimidazol-2-one The compound was purified by flash chromatography (cyclohexane-ethyl acetate 70-30). Thick oil.

[BB25]: N-(2-{3-[(2Z)-4-chloro-2-butenyl]-2-oxo-2,3-dihydro-1H-benzimidazol-1-yl]}ethyl)-acetamide The compound was purified by flash chromatography ($CH_2Cl_2$-methanol 97-3). Waxy solid from diisopropyl ether, m.p. 118° C.

[BB26]: N-(2-{3-[(2E)-4-Chloro-2-butenyl]-2-oxo-2,3-dihydro-1H-benzimidazol-1-yl]}ethyl)-acetamide White solid from diethyl ether, m.p. 108° C.

[BB13]: N-{2-[3-(2-Chloroethyl)-2-oxo-2,3-dihydro-1H-benzimidazol-1-yl]ethyl}methanesulfonamide The compound was purified by flash chromatography ($CH_2Cl_2$-methanol 98-2). White low melting solid.

[BB07]: N-{2-[3-(4-Chlorobutyl)-2-oxo-2,3-dihydro-1H-benzimidazol-1-yl]ethyl}methanesulfonamide White solid, m.p. 104° C. from diethyl ether.

[BB27]: N-(2-{3-[(2Z)-4-Chloro-2-butenyl)]-2-oxo-2,3-dihydro-1H-benzimidazol-1-yl]ethyl}methanesulfonamide The compound was purified by flash chromatography ($CH_2Cl_2$-methanol 97-3). White solid, m.p. 83° C. from diethyl ether.

[BB28]: N-2-{3-[(2E)-4-chloro-2butenyl)]-2-oxo-2,3-dihydro-1H-benzimidazol-1-yl]ethyl}methanesulfonamide The compound was purified by flash chromatography ($CH_2Cl_2$-methanol 98-2). White solid, m.p. 98° C. from diethyl ether.

Description 9

[BB08]: 1-(2-Chloroethyl)-3-[(2-piperidinyl)ethyl]-1,3-dihydro-2H-benzimidazol-2-one A solution of 1-[2-(1-piperidinyl)ethyl]-1,3-dihydro-2H-benzimidazol-2-one (4 g, 16.3 mmoles) in DMF (50 ml) was added to a suspension of 80% sodium hydride (0.49 g, 16.3 mmoles) in DMF (25 ml) and the reaction mixture was heated under stirring for 30 minutes at 40° C. The solution was slowly transferred (3 hours) into a solution of 1-bromo-2-chloroethane (2.7 ml, 32.6 mmoles) in DMF (30 ml), the temperature was increased to 60° C. and stirred for 5 hours. The reaction mixture was then taken to dryness under vacuum, and the residue partitioned between 5% aqueous HCl and diethyl ether. The aqueous layer was adjusted to pH 9 to 10 with sodium carbonate and extracted with ethyl acetate. After evaporation and flash chromatography purification ($CH_2Cl_2$-methanol-$NH_4OH$ 95-5-0.5), 2.2 g of the pure title compound was obtained as a clear oil.

According to the above described procedure, the following compounds were prepared from the suitable intermediates:

[BB02]: 1-(4-Chlorobutyl)-3-[(2-(1-piperidinyl)ethyl]-1,3-dihydro-2H-benzimidazol-2-one The compound was purified by flash chromatography ($CH_2Cl_2$-methanol-$NH_4OH$ 95-5-0.5). Ivory solid, m.p. 82° C.–87° C. from diethyl ether.

[BB12]: 1-(2-Chloroethyl)-3-[2-(4-morpholinyl)ethyl]-1,3-dihydro-2H-benzimidazol-2-one The compound was purified by flash chromatography ($CH_2Cl_2$-methanol-$NH_4OH$ 95-5-0.5). Thick oil.

[BB03]: 1-(4-Chlorobutyl)-3-[2-(4-morpholinyl)ethyl]-1,3-dihydro-2H-benzimidazol-2-one The compound was purified by flash chromatography ($CH_2Cl_2$-methanol-$NH_4OH$ 95-5-0.5). Clear oil.

Description 10

[BB14]: 1-[(2Z)-4-Chloro-2-butenyl)]-3-[2-(4-morpholinyl)ethyl]-1,3-dihydro-2H-benzimidazol-2-one A solution of 1-[2-(4-morpholinyl)ethyl]-1,3-dihydro-2H-benzimidazol-2-one (4 g, 16.2 mmoles) in DMF (50 ml) was added dropwise to a suspension of 80% sodium hydride (0.49 g, 16.2 mmoles) in DMF (50 ml) and the mixture was heated under stirring at 45° C. for 30 minutes. This solution was slowly transferred (4 hours) to a solution of cis-1,4-dichloro-2-butene (3.43 ml, 32.4 mmoles) in DMF (20 ml). The reaction mixture was stirred overnight at room temperature, taken to dryness under vacuum, and partitioned between ethyl acetate and water. From the organic solution after evaporation and flash chromatography purification ($CH_2Cl_2$-methanol-$NH_4OH$ 95-5-0.5), 2.4 g of the title compound were obtained as an oil.

According to the above described procedure, the following compounds were prepared from the suitable intermediates:

[BB19]: 1-[(2E)-4-Chloro-2-butenyl]-3-[2-(4-morpholinyl)ethyl]-1,3-dihydro-2H-benzimidazol-2-one The compound was purified by flash chromatography ($CH_2Cl_2$-methanol-$NH_4OH$ 95-5-0.5). Thick oil.

[BB17]: 1-[(2Z)-4-Chloro-2-butenyl]-3-[2-(1-piperidinyl)ethyl]-1,3-dihydro-2H-benzimidazol-2-one The compound was purified by flash chromatography ($CH_2Cl_2$-methanol-$NH_4OH$ 95-5-0.5). Thick oil.

[BB18]: 1-[(2E)-4-Chloro-2-butenyl]-3-[2-(1-piperidinyl)ethyl]-1,3-dihydro-2H-benzimidazol-2-one The compound was purified by flash chromatography ($CH_2Cl_2$-methanol-$NH_4OH$ 95-5-0.5). Thick oil.

Description 11

[BB10]: 1-(2-Chloroethyl)-3-(2-hydroxyethyl)-1,3-dihydro-2H-benzimidazol-2-one

A solution of 1-(2-chloroethyl)-3-[2-(tetrahydro-2H-pyran-2-yloxy)ethyl]-1,3-dihydro-2H-benzimidazol-2-one (2.2 g) and a catalytic amount of p-toluenesulfonic acid (0.1 g) in methanol (30 ml) was stirred at room temperature for 2 hours. The reaction mixture was evaporated to dryness, the residue was dissolved in $CH_2Cl_2$ and washed with a saturated aqueous solution of $K_2CO_3$. The organic layer was taken to dryness to give 1.5 g of the title compound as white solid. M.p. 135° C.

According to the above described procedure, the following compounds were prepared from the suitable intermediates:

[BB04]: 1-(4-Chlorobutyl)-3-(2-hydroxyethyl)-1,3-dihydro-2H-benzimidazol-2-one

Thick oil.

[BB20]: 1-[(2Z)-4-Chloro-2-butenyl]-3-(2-hydroxyethyl)-1,3-dihydro-2H-benzimidazol-2-one White solid, m.p. 80° C. from diethyl ether.

[BB21]: 1-[(2E)-4-Chloro-2-butenyl]-3-(2-hydroxyethyl)-1,3-dihydro-2H-benzimidazol-2-one Ivory solid, m.p. 73° C. from diethyl ether.

Description 12

[BB11]: 2-[3-(2-Chloroethyl)-2-oxo-2,3-dihydro-1H-benzimidazol-1-yl]ethyl-ethylcarbamate 1-(2-chloroethyl)-3-(2-hydroxyethyl)-1,3-dihydro-2H-benzimidazol-2-one (2.6 g, 11 mmoles) and ethyl isocyanate (20 ml) were refluxed under stirring for 6 hours then left overnight at room temperature. The reaction mixture was taken to dryness and the residue was crystallized from diisopropyl ether to give 3 g of the title compound. M.p. 125° C.

According to the above described procedure, the following compound was prepared from the suitable intermediate:

[BB05]: 2-[3-(4-Chlorobutyl)-2-oxo-2,3-dihydro-1H-benzimidazol-1-yl]ethyl-ethylcarbamate White solid, m.p. 75° C. from diethyl ether.

Description 13

[BB22]: 2-{3-[(2Z)-4-Chloro-2-butenyl]-2-oxo-2,3-dihydro-1H-benzimidazol-1-yl}ethyl-ethylcarbamate 1-(4-chlorobutyl)-3-(2-hydroxyethyl)-1,3-dihydro-2H-benzimidazol-2-one (1.8 g, 6.8 mmoles) and ethyl isocyanate (6 ml) were stirred at room temperature for 48 hours. The reaction mixture was then taken to dryness and the residue was crystallized from diethyl ether to give 1.8 g the title compound. M.p. 107° C.

According to the above described procedure, the following compound was prepared from the suitable intermediate:

[BB23]: 2-{3-[(2E)-4-Chloro-2-butenyl]-2-oxo-2,3-dihydro-1H-benzimidazol-1-yl}ethyl-ethylcarbamate The compound was purified by flash chromatography (cyclohexane-ethyl acetate 50-50). White solid, m.p. 70° C. from diethyl ether.

B. General Method for the Preparation of the Compounds of Formula (I)

A solution of each building block of formula (II) (0.1 mM) was reacted under stirring with each amine (0.2 mM) in anhydrous DMF (100 μl) in the presence of $Na_2CO_3$ (0.3 mM) at a temperature ranging from room temperature to 100° C., preferably between 60° C. and 80° C., for about 6 to 8 hours. Isocyanatemethyl Polystyrene Resin (loading 0.23 meq/g) (0.2 mM) was introduced and the mixture was gently stirred at room temperature for 8 hours. The resin was then filtered off under vacuum, washed with DMF, and filtered again. The collected solutions were evaporated to dryness in a speed-vac centrifuge. The compounds which were prepared according to the above described procedure are listed in Table 3.

Table 3 collects the structural formula of the synthesized compounds along with the corresponding characterizing mass data (i.e., $[M+H]^+$) obtained for each of the compounds according to the invention. The identification of the compounds and their purity was carried out by using positive APCI-LC/MS technique.

TABLE 3

Compounds of Formula (I)

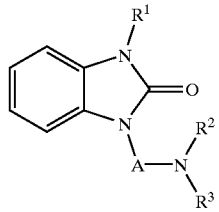

(I)

| Compound No. | —$R^1$ | —A— |  | $[M + H]^+$ |
|---|---|---|---|---|
| 1 | ⁀⁀OMe | ⁀⁀⁀ | —N‿N—Ph | 409 |
| 2 | ⁀⁀OMe | ⁀⁀⁀⁀ | —N‿N—CH(Ph)(4-Cl-C6H4) | 533 |

TABLE 3-continued

Compounds of Formula (I)

| Compound No. | —R¹ | —A— | —N(R²)(R³) | [M + H]⁺ |
|---|---|---|---|---|
| 3 | propyl-OMe | pentylene | piperazinyl-N-benzyl | 423 |
| 4 | propyl-OMe | pentylene | piperazinyl-(2-pyridyl) | 410 |
| 5 | propyl-OMe | pentylene | piperazinyl-(3-chlorophenyl) | 443 |
| 6 | propyl-OMe | pentylene | piperazinyl-(2-pyrimidyl) | 411 |
| 7 | propyl-OMe | pentylene | 2-methyl-1,2,3,4-tetrahydro-β-carbolin-2-yl | 419 |
| 8 | propyl-OMe | pentylene | piperazinyl-(3,5-dichloropyridin-4-yl) | 478 |
| 9 | propyl-OMe | pentylene | piperazinyl-(3-trifluoromethylphenyl) | 477 |
| 10 | propyl-OMe | pentylene | 4-phenyl-1,2,3,6-tetrahydropyridin-1-yl | 406 |
| 11 | propyl-OMe | pentylene | piperazinyl-(3,4-dichlorophenyl) | 477 |

TABLE 3-continued

Compounds of Formula (I)

| Compound No. | —R¹ | —A— | —N(R²)(R³) | [M + H]⁺ |
|---|---|---|---|---|
| 12 | CH₂CH₂CH₂OMe | (CH₂)₅ | 4-(1-methylpiperidin-4-yl)-2,3-dihydro-1H-benzimidazol-2-one linked via piperidine N | 464 |
| 13 | CH₂CH₂CH₂OMe | (CH₂)₅ | 4-(4-chloro-3-trifluoromethylphenyl)-4-hydroxy-1-methylpiperidine | 526 |
| 14 | CH₂CH₂CH₂OMe | (CH₂)₅ | 1-methyl-4-(4-methoxyphenyl)piperazine | 439 |
| 15 | CH₂CH₂CH₂OMe | (CH₂)₅ | 1-methyl-4-(4-chlorobenzyl)piperazine | 457 |
| 16 | CH₂CH₂CH₂OMe | (CH₂)₅ | 8-methyl-1-phenyl-1,3,8-triazaspiro[4.5]decan-4-one | 478 |
| 17 | CH₂CH₂CH₂OMe | (CH₂)₅ | 1-methyl-4-(1,3-benzodioxol-5-ylmethyl)piperazine | 467 |

TABLE 3-continued

Compounds of Formula (I)

| Compound No. | —R¹ | —A— | —N(R²)(R³) | [M + H]⁺ |
|---|---|---|---|---|
| 18 | propyl-OMe | hexyl | piperazinyl-(2,3-dimethylphenyl) | 437 |
| 19 | propyl-OMe | hexyl | piperazinyl-(2-methoxyphenyl) | 439 |
| 20 | propyl-piperidinyl | hexyl | piperazinyl-Ph | 462 |
| 21 | propyl-piperidinyl | hexyl | piperazinyl-CH(Ph)(4-chlorophenyl) | 586 |
| 22 | propyl-piperidinyl | hexyl | piperazinyl-N-benzyl | 476 |
| 23 | propyl-piperidinyl | hexyl | piperazinyl-(2-pyridyl) | 463 |
| 24 | propyl-piperidinyl | hexyl | piperazinyl-(3-chlorophenyl) | 496 |
| 25 | propyl-piperidinyl | hexyl | piperazinyl-(2-pyrimidinyl) | 464 |
| 26 | propyl-piperidinyl | hexyl | 2,3,4,9-tetrahydro-1H-β-carbolin-2-yl | 472 |

TABLE 3-continued
Compounds of Formula (I)
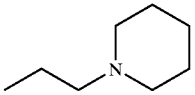
(I)
| Compound No. | —R¹ | —A— | —N(R²)(R³) | [M + H]⁺ |
|---|---|---|---|---|
| 27 | 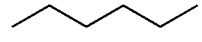 | 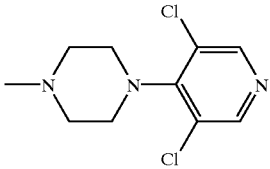 | 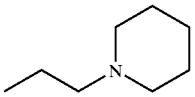 | 531 |
| 28 | 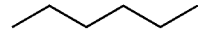 | 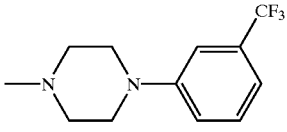 | 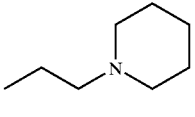 | 530 |
| 29 |  | 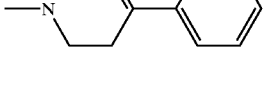 | 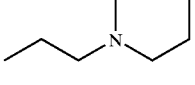 | 459 |
| 30 |  | 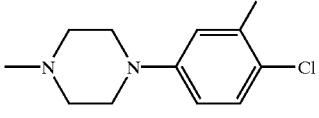 | 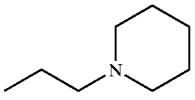 | 530 |
| 31 |  | 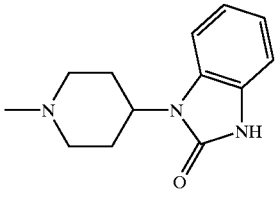 | 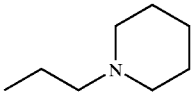 | 517 |
| 32 | 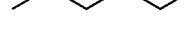 | 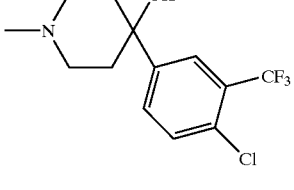 | 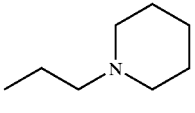 | 579 |
| 33 |  | | 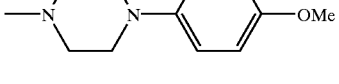 | 492 |

TABLE 3-continued

Compounds of Formula (I)

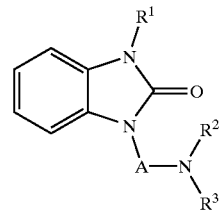

(I)

| Compound No. | —R¹ | —A— | —N(R²)(R³) | [M + H]⁺ |
|---|---|---|---|---|
| 34 | propyl-piperidine | hexyl | 4-methylpiperazinyl-CH₂-(4-chlorophenyl) | 510 |
| 35 | propyl-piperidine | hexyl | 1-phenyl-4-oxo-1,3,8-triazaspiro[4.5]decan-8-yl | 531 |
| 36 | propyl-piperidine | hexyl | 4-methylpiperazinyl-CH₂-(benzo[1,3]dioxol-5-yl) | 520 |
| 37 | propyl-piperidine | hexyl | 4-(2,3-dimethylphenyl)piperazinyl | 490 |
| 38 | propyl-piperidine | hexyl | 4-(2-methoxyphenyl)piperazinyl | 492 |
| 39 | propyl-morpholine | hexyl | 4-phenylpiperazinyl | 464 |
| 40 | propyl-morpholine | hexyl | 4-[(4-chlorophenyl)(phenyl)methyl]piperazinyl | 588 |

TABLE 3-continued

Compounds of Formula (I)

| Compound No. | —R¹ | —A— | —N(R²)(R³) | [M + H]⁺ |
|---|---|---|---|---|
| 41 | propyl-morpholine | pentyl | 4-benzyl-piperazin-1-yl | 478 |
| 42 | propyl-morpholine | pentyl | 4-(pyridin-2-yl)piperazin-1-yl | 465 |
| 43 | propyl-morpholine | pentyl | 4-(3-chlorophenyl)piperazin-1-yl | 498 |
| 44 | propyl-morpholine | pentyl | 4-(pyrimidin-2-yl)piperazin-1-yl | 466 |
| 45 | propyl-morpholine | pentyl | 2-methyl-2,3,4,9-tetrahydro-1H-β-carbolin-2-yl | 474 |
| 46 | propyl-morpholine | pentyl | 4-(3,5-dichloropyridin-4-yl)piperazin-1-yl | 533 |
| 47 | propyl-morpholine | pentyl | 4-(3-trifluoromethylphenyl)piperazin-1-yl | 532 |
| 48 | propyl-morpholine | pentyl | 4-phenyl-1,2,3,6-tetrahydropyridin-1-yl | 461 |
| 49 | propyl-morpholine | pentyl | 4-(3,4-dichlorophenyl)piperazin-1-yl | 532 |

TABLE 3-continued

Compounds of Formula (I)

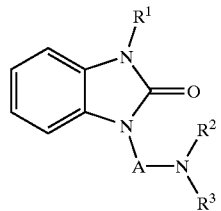

| Compound No. | —R¹ | —A— | —N(R²)(R³) | [M + H]⁺ |
|---|---|---|---|---|
| 50 | propyl-morpholine | hexyl | 1-methylpiperidin-4-yl-(benzimidazol-2(3H)-one) | 519 |
| 51 | propyl-morpholine | hexyl | 1-methyl-4-hydroxy-4-(4-chloro-3-trifluoromethylphenyl)piperidine | 581 |
| 52 | propyl-morpholine | hexyl | 4-(4-methoxyphenyl)-1-methylpiperazine | 494 |
| 53 | propyl-morpholine | hexyl | 4-(4-chlorobenzyl)-1-methylpiperazine | 512 |
| 54 | propyl-morpholine | hexyl | 1-phenyl-8-methyl-1,3,8-triazaspiro[4.5]decan-4-one | 533 |
| 55 | propyl-morpholine | hexyl | 4-(1,3-benzodioxol-5-ylmethyl)-1-methylpiperazine | 522 |
| 56 | propanol | hexyl | 4-phenyl-1-methylpiperazine | 395 |

TABLE 3-continued

Compounds of Formula (I)

| Compound No. | —R¹ | —A— | —N(R²)(R³) | [M + H]⁺ |
|---|---|---|---|---|
| 57 | propyl-OH | hexyl | piperazine-CH(Ph)(4-chlorophenyl) | 419 |
| 58 | propyl-OH | hexyl | piperazine-N-benzyl | 409 |
| 59 | propyl-OH | hexyl | piperazine-(2-pyridyl) | 396 |
| 60 | propyl-OH | hexyl | piperazine-(3-chlorophenyl) | 429 |
| 61 | propyl-OH | hexyl | piperazine-(2-pyrimidinyl) | 397 |
| 62 | propyl-OH | hexyl | 2,3,4,9-tetrahydro-1H-β-carbolin-2-yl | 405 |
| 63 | propyl-OH | hexyl | piperazine-(3,5-dichloro-4-pyridyl) | 464 |
| 64 | propyl-OH | hexyl | piperazine-(3-trifluoromethylphenyl) | 463 |

TABLE 3-continued

Compounds of Formula (I)

| Compound No. | —R¹ | —A— | —N(R²)(R³) | [M + H]⁺ |
|---|---|---|---|---|
| 65 | propyl-OH | hexyl | N-methyl-4-phenyl-1,2,3,6-tetrahydropyridine | 392 |
| 66 | propyl-OH | hexyl | 4-(3,4-dichlorophenyl)-1-methylpiperazine | 463 |
| 67 | propyl-OH | hexyl | 1-(1-methylpiperidin-4-yl)-1,3-dihydro-2H-benzimidazol-2-one | 450 |
| 68 | propyl-OH | hexyl | 4-(4-chloro-3-trifluoromethylphenyl)-4-hydroxy-1-methylpiperidine | 512 |
| 69 | propyl-OH | hexyl | 4-(4-methoxyphenyl)-1-methylpiperazine | 425 |
| 70 | propyl-OH | hexyl | 4-(4-chlorobenzyl)-1-methylpiperazine | 443 |
| 71 | propyl-OH | hexyl | 8-methyl-1-phenyl-1,3,8-triazaspiro[4.5]decan-4-one | 464 |

TABLE 3-continued

Compounds of Formula (I)

| Compound No. | —R¹ | —A— | —N(R²)(R³) | [M + H]⁺ |
|---|---|---|---|---|
| 72 | propyl-OH | hexyl | piperazinyl-CH₂-(benzo[1,3]dioxol-5-yl) | 453 |
| 73 | propyl-OH | hexyl | piperazinyl-(2,3-dimethylphenyl) | 423 |
| 74 | propyl-OH | hexyl | piperazinyl-(2-methoxyphenyl) | 425 |
| 75 | propyl-O-C(O)-NHEthyl | hexyl | piperazinyl-Ph | 466 |
| 76 | propyl-O-C(O)-NHEthyl | hexyl | piperazinyl-CH(Ph)(4-chlorophenyl) | 590 |
| 77 | propyl-O-C(O)-NHEthyl | hexyl | piperazinyl-N-benzyl | 480 |
| 78 | propyl-O-C(O)-NHEthyl | hexyl | piperazinyl-(2-pyridyl) | 467 |
| 79 | propyl-O-C(O)-NHEthyl | hexyl | piperazinyl-(3-chlorophenyl) | 500 |

TABLE 3-continued

Compounds of Formula (I)

| Compound No. | —R¹ | —A— | —N(R²)(R³) | [M + H]⁺ |
|---|---|---|---|---|
| 80 | propyl-O-C(O)-NHEthyl | pentyl | piperazinyl-pyrimidin-2-yl | 468 |
| 81 | propyl-O-C(O)-NHEthyl | pentyl | 2-methyl-1,2,3,4-tetrahydro-β-carbolin-2-yl | 476 |
| 82 | propyl-O-C(O)-NHEthyl | pentyl | 4-(3,5-dichloropyridin-4-yl)piperazin-1-yl | 535 |
| 83 | propyl-O-C(O)-NHEthyl | pentyl | 4-(3-trifluoromethylphenyl)piperazin-1-yl | 534 |
| 84 | propyl-O-C(O)-NHEthyl | pentyl | 4-phenyl-1,2,3,6-tetrahydropyridin-1-yl | 463 |
| 85 | propyl-O-C(O)-NHEthyl | pentyl | 4-(3,4-dichlorophenyl)piperazin-1-yl | 534 |
| 86 | propyl-O-C(O)-NHEthyl | pentyl | 4-(2-oxo-2,3-dihydro-1H-benzimidazol-1-yl)piperidin-1-yl | 521 |
| 87 | propyl-O-C(O)-NHEthyl | pentyl | 4-(4-chloro-3-trifluoromethylphenyl)-4-hydroxypiperidin-1-yl | 583 |

TABLE 3-continued

Compounds of Formula (I)

(I)

| Compound No. | —R¹ | —A— | —N(R²)(R³) | [M + H]⁺ |
|---|---|---|---|---|
| 88 | propyl-O-C(O)-NHEthyl | pentyl | N-methylpiperazine-N'-(4-methoxyphenyl) | 496 |
| 89 | propyl-O-C(O)-NHEthyl | pentyl | N-methylpiperazine-N'-(4-chlorobenzyl) | 514 |
| 90 | propyl-O-C(O)-NHEthyl | pentyl | 1-phenyl-4-oxo-1,3,8-triazaspiro[4.5]decan-8-yl (N-methyl) | 535 |
| 91 | propyl-O-C(O)-NHEthyl | pentyl | N-methylpiperazine-N'-(benzo[1,3]dioxol-5-ylmethyl) | 524 |
| 92 | propyl-O-C(O)-NHEthyl | pentyl | N-methylpiperazine-N'-(2,3-dimethylphenyl) | 494 |
| 93 | propyl-O-C(O)-NHEthyl | pentyl | N-methylpiperazine-N'-(2-methoxyphenyl) | 496 |
| 94 | propyl-O-C(O)-NHEthyl | pentyl | N-methylpiperazine-N'-(3-methylphenyl) | 480 |

TABLE 3-continued

Compounds of Formula (I)

| Compound No. | —R¹ | —A— | —N(R²)(R³) | [M + H]⁺ |
|---|---|---|---|---|
| 95 | propyl-O-C(O)-NHEthyl | pentylene | piperazinyl-(2-methylphenyl) | 480 |
| 96 | propyl-O-C(O)-NHEthyl | pentylene | piperazinyl-(2-chlorophenyl) | 500 |
| 97 | propyl-NH-C(O)-CH₃ | pentylene | piperazinyl-Ph | 436 |
| 98 | propyl-NH-C(O)-CH₃ | pentylene | piperazinyl-CH(Ph)(4-chlorophenyl) | 560 |
| 99 | propyl-NH-C(O)-CH₃ | pentylene | piperazinyl-N-benzyl | 450 |
| 100 | propyl-NH-C(O)-CH₃ | pentylene | piperazinyl-(2-pyridyl) | 437 |
| 101 | propyl-NH-C(O)-CH₃ | pentylene | piperazinyl-(3-chlorophenyl) | 470 |
| 102 | propyl-NH-C(O)-CH₃ | pentylene | piperazinyl-(2-pyrimidinyl) | 438 |

TABLE 3-continued
Compounds of Formula (I)
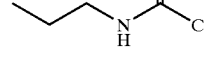
(I)
| Compound No. | —R¹ | —A— | —N(R²)R³ | [M + H]⁺ |
|---|---|---|---|---|
| 103 |  | 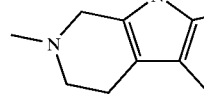 |  | 446 |
| 104 | 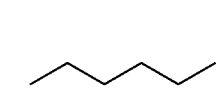 |  |  | 505 |
| 105 | 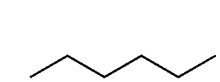 | 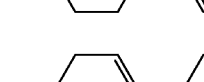 | 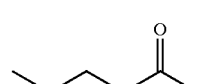 | 504 |
| 106 | 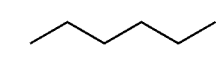 |  | 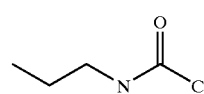 | 433 |
| 107 | 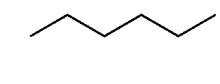 |  |  | 504 |
| 108 | 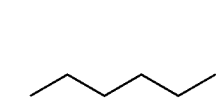 |  |  | 491 |
| 109 |  |  | | 553 |

US 6,521,623 B1
53 54
TABLE 3-continued
Compounds of Formula (I)
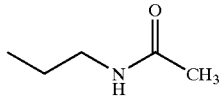
(I)
| Compound No. | —R¹ | —A— | —N(R²)(R³) | [M + H]⁺ |
|---|---|---|---|---|
| 110 |  | 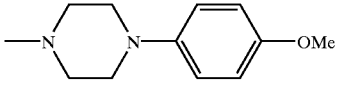 | 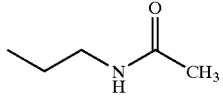 | 466 |
| 111 |  | 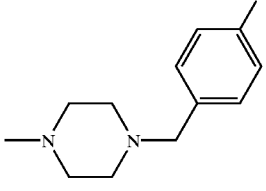 | 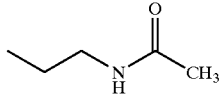 | 484 |
| 112 |  | 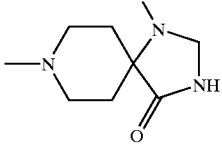 | 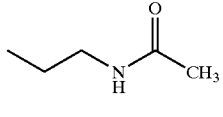 | 505 |
| 113 |  | 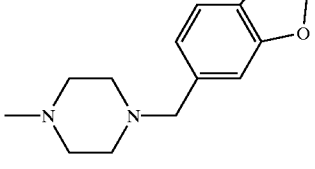 | 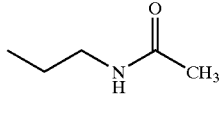 | 494 |
| 114 |  | 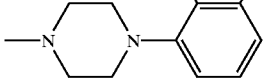 | 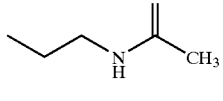 | 464 |
| 115 |  | 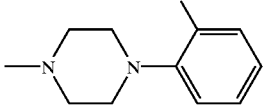 | 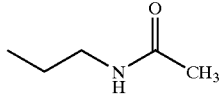 | 466 |
| 116 |  | 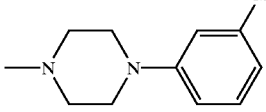 | | 450 |

TABLE 3-continued

Compounds of Formula (I)

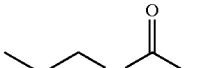

| Compound No. | —R¹ | —A— | —N(R²)(R³) | [M + H]⁺ |
|---|---|---|---|---|
| 117 | propyl-NHC(O)CH₃ | hexylene | 4-(2-methylphenyl)piperazin-1-yl | 450 |
| 118 | propyl-NHC(O)CH₃ | hexylene | 4-(2-chlorophenyl)piperazin-1-yl | 470 |
| 119 | propyl-NHSO₂CH₃ | hexylene | 4-phenylpiperazin-1-yl | 472 |
| 120 | propyl-NHSO₂CH₃ | hexylene | 4-[(4-chlorophenyl)(phenyl)methyl]piperazin-1-yl | 596 |
| 121 | propyl-NHSO₂CH₃ | hexylene | 4-benzylpiperazin-1-yl | 486 |
| 122 | propyl-NHSO₂CH₃ | hexylene | 4-(pyridin-2-yl)piperazin-1-yl | 473 |
| 123 | propyl-NHSO₂CH₃ | hexylene | 4-(3-chlorophenyl)piperazin-1-yl | 506 |
| 124 | propyl-NHSO₂CH₃ | hexylene | 4-(pyrimidin-2-yl)piperazin-1-yl | 474 |
| 125 | propyl-NHSO₂CH₃ | hexylene | 2,3,4,9-tetrahydro-1H-β-carbolin-2-yl | 482 |

TABLE 3-continued

Compounds of Formula (I)

| Compound No. | —R¹ | —A— | —N(R²)(R³) | [M + H]⁺ |
|---|---|---|---|---|
| 126 | ~NHSO₂CH₃ | (pentyl chain) | piperazine-N-(3,5-dichloropyridin-4-yl) | 541 |
| 127 | ~NHSO₂CH₃ | (pentyl chain) | piperazine-N-(3-trifluoromethylphenyl) | 540 |
| 128 | ~NHSO₂CH₃ | (pentyl chain) | 4-phenyl-1,2,3,6-tetrahydropyridine | 469 |
| 129 | ~NHSO₂CH₃ | (pentyl chain) | piperazine-N-(3,4-dichlorophenyl) | 540 |
| 130 | ~NHSO₂CH₃ | (pentyl chain) | 4-(2-oxo-2,3-dihydro-1H-benzimidazol-1-yl)piperidine | 527 |
| 131 | ~NHSO₂CH₃ | (pentyl chain) | 4-hydroxy-4-(4-chloro-3-trifluoromethylphenyl)piperidine | 589 |
| 132 | ~NHSO₂CH₃ | (pentyl chain) | piperazine-N-(4-methoxyphenyl) | 502 |

TABLE 3-continued

Compounds of Formula (I)

| Compound No. | —R¹ | —A— | —N(R²)(R³) | [M + H]⁺ |
|---|---|---|---|---|
| 133 | propyl-NHSO₂CH₃ | pentyl | 4-(4-chlorobenzyl)piperazin-1-yl | 520 |
| 134 | propyl-NHSO₂CH₃ | pentyl | 1-phenyl-8-methyl-1,3,8-triazaspiro[4.5]decan-4-one-3-yl | 541 |
| 135 | propyl-NHSO₂CH₃ | pentyl | 4-(1,3-benzodioxol-5-ylmethyl)piperazin-1-yl | 530 |
| 136 | propyl-NHSO₂CH₃ | pentyl | 4-(2,3-dimethylphenyl)piperazin-1-yl | 500 |
| 137 | propyl-NHSO₂CH₃ | pentyl | 4-(2-methoxyphenyl)piperazin-1-yl | 502 |
| 138 | propyl-NHSO₂CH₃ | pentyl | 4-(3-methylphenyl)piperazin-1-yl | 486 |
| 139 | propyl-NHSO₂CH₃ | pentyl | 4-(2-methylphenyl)piperazin-1-yl | 486 |

TABLE 3-continued

Compounds of Formula (I)

| Compound No. | —R¹ | —A— | —N(R²)(R³) | [M + H]⁺ |
|---|---|---|---|---|
| 140 | ~NHSO₂CH₃ | hexyl | 4-(2-chlorophenyl)piperazin-1-yl | 506 |
| 141 | 3-(piperidin-1-yl)propyl | butyl | 4-phenylpiperazin-1-yl | 434 |
| 142 | 3-(piperidin-1-yl)propyl | butyl | 4-[(4-chlorophenyl)(phenyl)methyl]piperazin-1-yl | 558 |
| 143 | 3-(piperidin-1-yl)propyl | butyl | 4-benzylpiperazin-1-yl | 448 |
| 144 | 3-(piperidin-1-yl)propyl | butyl | 4-(pyridin-2-yl)piperazin-1-yl | 435 |
| 145 | 3-(piperidin-1-yl)propyl | butyl | 4-(3-chlorophenyl)piperazin-1-yl | 468 |
| 146 | 3-(piperidin-1-yl)propyl | butyl | 4-(pyrimidin-2-yl)piperazin-1-yl | 436 |
| 147 | 3-(piperidin-1-yl)propyl | butyl | 2-methyl-2,3,4,9-tetrahydro-1H-β-carbolin-2-yl | 444 |

TABLE 3-continued

Compounds of Formula (I)

| Compound No. | —R¹ | —A— | —N(R²)(R³) | [M + H]⁺ |
|---|---|---|---|---|
| 148 | propyl-piperidine | butyl | N-methylpiperazinyl-3,5-dichloropyridin-4-yl | 503 |
| 149 | propyl-piperidine | butyl | N-methylpiperazinyl-3-(trifluoromethyl)phenyl | 502 |
| 150 | propyl-piperidine | butyl | 4-phenyl-1,2,3,6-tetrahydropyridin-1-yl | 431 |
| 151 | propyl-piperidine | butyl | N-methylpiperazinyl-3,4-dichlorophenyl | 502 |
| 152 | propyl-piperidine | butyl | 1-(2-oxo-2,3-dihydro-1H-benzimidazol-1-yl)piperidin-4-yl | 489 |
| 153 | propyl-piperidine | butyl | 4-hydroxy-4-[4-chloro-3-(trifluoromethyl)phenyl]piperidin-1-yl | 551 |
| 154 | propyl-piperidine | butyl | N-methylpiperazinyl-4-methoxyphenyl | 464 |

TABLE 3-continued

Compounds of Formula (I)

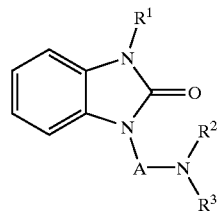

| Compound No. | —R¹ | —A— | —N(R²)(R³) | [M + H]⁺ |
|---|---|---|---|---|
| 155 | propyl-piperidine | butylene | N-methylpiperazinyl-CH₂-(4-chlorophenyl) | 482 |
| 156 | propyl-piperidine | butylene | 1-phenyl-4-methyl-1,3,8-triazaspiro[4.5]decan-2-one | 503 |
| 157 | propyl-piperidine | butylene | N-methylpiperazinyl-CH₂-(3,4-methylenedioxyphenyl) | 492 |
| 158 | propyl-piperidine | butylene | N-methylpiperazinyl-(2,3-dimethylphenyl) | 462 |
| 159 | propyl-piperidine | butylene | N-methylpiperazinyl-(2-methoxyphenyl) | 464 |
| 160 | CH₂CH₂CH₂OMe | butylene | N-methylpiperazinyl-Ph | 381 |
| 161 | CH₂CH₂CH₂OMe | butylene | N-methylpiperazinyl-CH(Ph)(4-chlorophenyl) | 505 |

TABLE 3-continued

Compounds of Formula (I)

(I)

| Compound No. | —R¹ | —A— | —N(R²)(R³) | [M + H]⁺ |
|---|---|---|---|---|
| 162 | CH₂CH₂CH₂OMe | CH₂CH₂CH₂ | piperazinyl-N-benzyl | 395 |
| 163 | CH₂CH₂CH₂OMe | CH₂CH₂CH₂ | 4-(pyridin-2-yl)piperazin-1-yl | 382 |
| 164 | CH₂CH₂CH₂OMe | CH₂CH₂CH₂ | 4-(3-chlorophenyl)piperazin-1-yl | 415 |
| 165 | CH₂CH₂CH₂OMe | CH₂CH₂CH₂ | 4-(pyrimidin-2-yl)piperazin-1-yl | 383 |
| 166 | CH₂CH₂CH₂OMe | CH₂CH₂CH₂ | 2-methyl-1,2,3,4-tetrahydro-β-carbolin-2-yl | 391 |
| 167 | CH₂CH₂CH₂OMe | CH₂CH₂CH₂ | 4-(3,5-dichloropyridin-4-yl)piperazin-1-yl | 450 |
| 168 | CH₂CH₂CH₂OMe | CH₂CH₂CH₂ | 4-(3-trifluoromethylphenyl)piperazin-1-yl | 449 |
| 169 | CH₂CH₂CH₂OMe | CH₂CH₂CH₂ | 4-phenyl-1,2,3,6-tetrahydropyridin-1-yl | 378 |
| 170 | CH₂CH₂CH₂OMe | CH₂CH₂CH₂ | 4-(3,4-dichlorophenyl)piperazin-1-yl | 449 |

TABLE 3-continued

Compounds of Formula (I)

| Compound No. | —R¹ | —A— | —N(R²)(R³) | [M + H]⁺ |
|---|---|---|---|---|
| 171 | CH₂CH₂CH₂OMe | CH₂CH₂CH₂ | 1-methylpiperidin-4-yl attached to benzimidazol-2(3H)-one NH | 436 |
| 172 | CH₂CH₂CH₂OMe | CH₂CH₂CH₂ | 1-methyl-4-(4-chloro-3-trifluoromethylphenyl)-4-hydroxypiperidin-1-yl | 526 |
| 173 | CH₂CH₂CH₂OMe | CH₂CH₂CH₂ | 4-(4-methoxyphenyl)-1-methylpiperazin-1-yl | 411 |
| 174 | CH₂CH₂CH₂OMe | CH₂CH₂CH₂ | 4-(4-chlorobenzyl)-1-methylpiperazin-1-yl | 429 |
| 175 | CH₂CH₂CH₂OMe | CH₂CH₂CH₂ | 8-methyl-1-phenyl-1,3,8-triazaspiro[4.5]decan-4-one-8-yl | 450 |
| 176 | CH₂CH₂CH₂OMe | CH₂CH₂CH₂ | 4-(1,3-benzodioxol-5-ylmethyl)-1-methylpiperazin-1-yl | 450 |

TABLE 3-continued
Compounds of Formula (I)
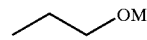
(I)
| Compound No. | —R¹ | —A— | $-N\begin{subarray}{l}R^2\\ R^3\end{subarray}$ | [M + H]⁺ |
|---|---|---|---|---|
| 177 |  OMe |  | 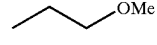 | 409 |
| 178 |  OMe |  |  | 411 |
| 179 |  OH | 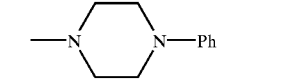 |  | 367 |
| 180 |  OH |  |  | 491 |
| 181 |  OH | 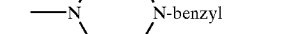 |  | 381 |
| 182 |  OH |  |  | 368 |
| 183 | 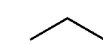 OH | 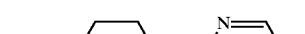 |  | 401 |
| 184 |  OH | 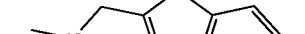 |  | 369 |
| 185 |  OH |  | | 377 |

TABLE 3-continued

Compounds of Formula (I)

| Compound No. | —R¹ | —A— | —N(R²)(R³) | [M + H]⁺ |
|---|---|---|---|---|
| 186 | propyl-OH | butyl | 4-(3,5-dichloropyridin-4-yl)piperazin-1-yl | 436 |
| 187 | propyl-OH | butyl | 4-(3-trifluoromethylphenyl)piperazin-1-yl | 435 |
| 188 | propyl-OH | butyl | 4-phenyl-1,2,3,6-tetrahydropyridin-1-yl | 364 |
| 189 | propyl-OH | butyl | 4-(3,4-dichlorophenyl)piperazin-1-yl | 435 |
| 190 | propyl-OH | butyl | 4-(2-oxo-2,3-dihydro-1H-benzimidazol-1-yl)piperidin-1-yl | 422 |
| 191 | propyl-OH | butyl | 4-(4-chloro-3-trifluoromethylphenyl)-4-hydroxypiperidin-1-yl | 484 |
| 192 | propyl-OH | butyl | 4-(4-methoxyphenyl)piperazin-1-yl | 397 |

TABLE 3-continued

Compounds of Formula (I)

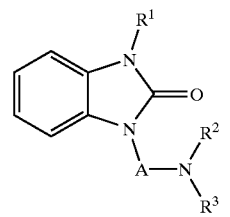

(I)

| Compound No. | —R¹ | —A— | —N(R²)(R³) | [M + H]⁺ |
|---|---|---|---|---|
| 193 | propyl-OH | butylene | 4-(4-chlorobenzyl)piperazin-1-yl | 415 |
| 194 | propyl-OH | butylene | 1-phenyl-8-methyl-4-oxo-1,3,8-triazaspiro[4.5]decan-3-yl (via piperazine N) | 436 |
| 195 | propyl-OH | butylene | 4-(1,3-benzodioxol-5-ylmethyl)piperazin-1-yl | 436 |
| 196 | propyl-OH | butylene | 4-(2,3-dimethylphenyl)piperazin-1-yl | 395 |
| 197 | propyl-OH | butylene | 4-(2-methoxyphenyl)piperazin-1-yl | 397 |
| 198 | CH₂CH₂CH₂-O-C(=O)-NHEthyl | butylene | 4-phenylpiperazin-1-yl | 438 |
| 199 | CH₂CH₂CH₂-O-C(=O)-NHEthyl | butylene | 4-[(4-chlorophenyl)(phenyl)methyl]piperazin-1-yl | 562 |

TABLE 3-continued
Compounds of Formula (I)
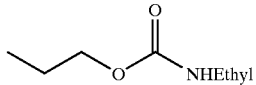
(I)
| Compound No. | —R¹ | —A— | —N(R²)(R³) | [M + H]⁺ |
|---|---|---|---|---|
| 200 |  | 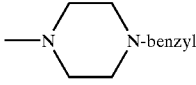 | 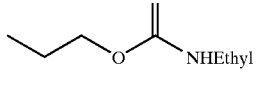 | 452 |
| 201 |  | 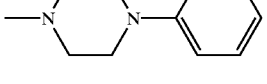 | 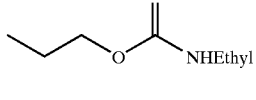 | 439 |
| 202 |  | 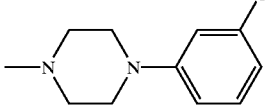 | 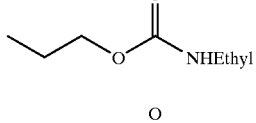 | 472 |
| 203 |  | 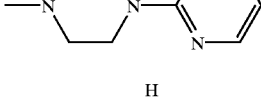 | 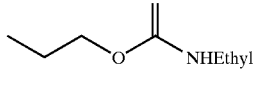 | 440 |
| 204 |  | 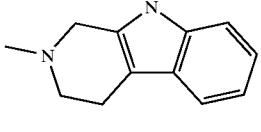 | 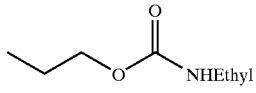 | 448 |
| 205 |  | 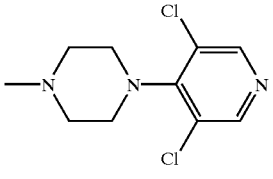 | 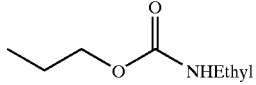 | 507 |
| 206 |  | 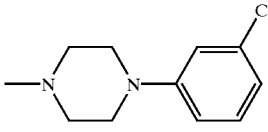 | 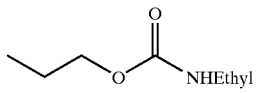 | 506 |
| 207 |  | 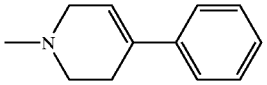 | 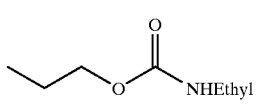 | 435 |
| 208 |  | 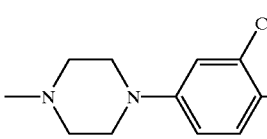 | | 506 |

TABLE 3-continued
Compounds of Formula (I)
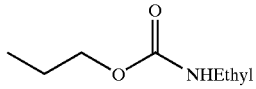
| Compound No. | —R¹ | —A— | —N(R²)(R³) | [M + H]⁺ |
|---|---|---|---|---|
| 209 | 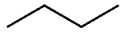 | 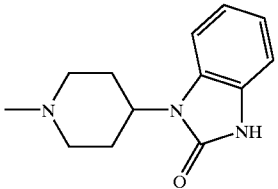 | 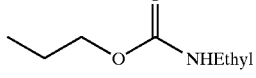 | 493 |
| 210 | 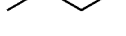 | 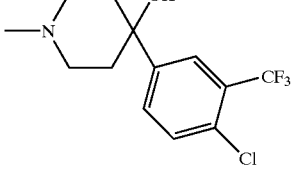 | 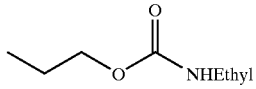 | 555 |
| 211 | 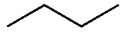 | 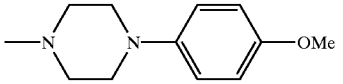 | 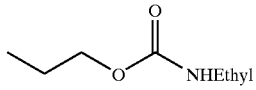 | 468 |
| 212 | 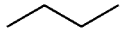 | 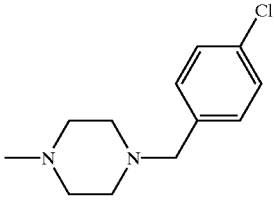 | 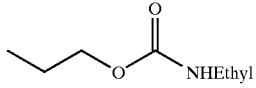 | 486 |
| 213 | 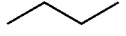 | 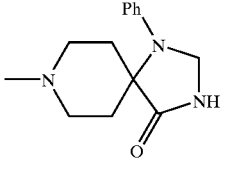 | 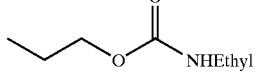 | 507 |
| 214 | 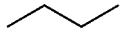 | | 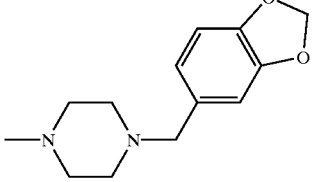 | 496 |

TABLE 3-continued
Compounds of Formula (I)
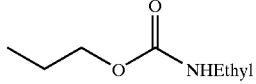
| Compound No. | —R¹ | —A— | —N(R²)(R³) | [M + H]⁺ |
|---|---|---|---|---|
| 215 |  | 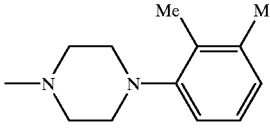 | 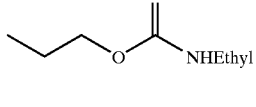 | 466 |
| 216 |  | 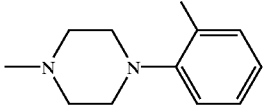 | 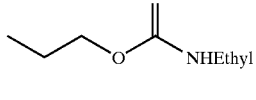 | 468 |
| 217 |  | 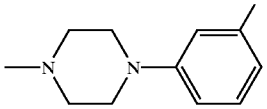 | 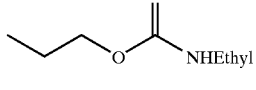 | 452 |
| 218 |  | 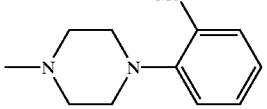 | 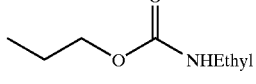 | 452 |
| 219 |  | 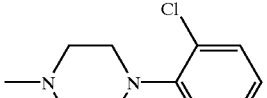 | 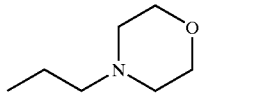 | 472 |
| 220 |  | 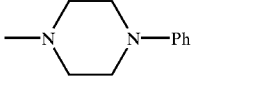 | 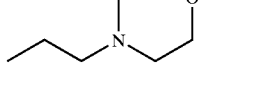 | 436 |
| 221 |  | 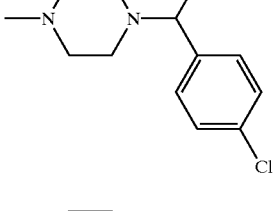 | 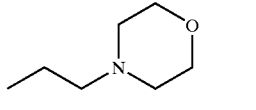 | 560 |
| 222 |  | 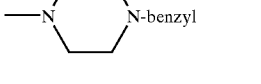 | —N(piperazine)N-benzyl | 450 |

TABLE 3-continued
Compounds of Formula (I)
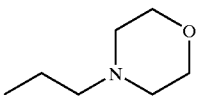
| Compound No. | —R¹ | —A— | —N(R²)(R³) | [M + H]⁺ |
|---|---|---|---|---|
| 223 | 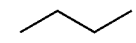 | 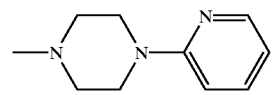 | 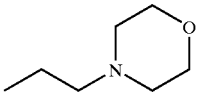 | 437 |
| 224 | 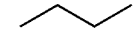 | 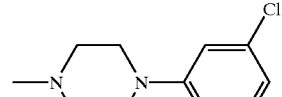 | 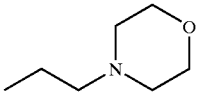 | 470 |
| 225 | 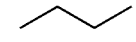 | 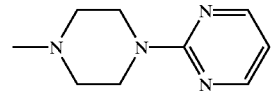 | 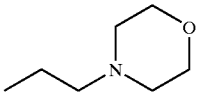 | 438 |
| 226 |  | 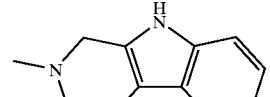 | 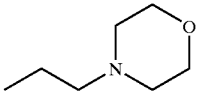 | 446 |
| 227 | 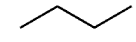 | 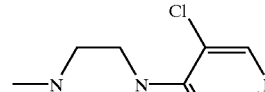 |  | 533 |
| 228 |  | 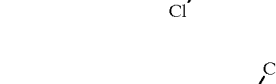 |  | 504 |
| 229 |  | 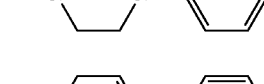 | 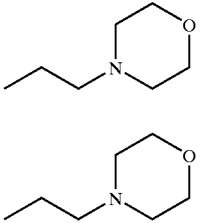 | 433 |
| 230 |  | |  | 504 |

TABLE 3-continued
Compounds of Formula (I)
| Compound No. | —R¹ | —A— | —N(R²)(R³) | [M + H]⁺ |
|---|---|---|---|---|
| 231 |  |  | 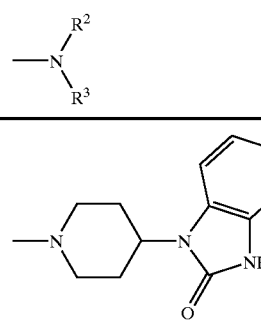 | 491 |
| 232 |  |  | 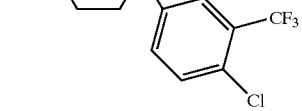 | 553 |
| 233 |  |  | 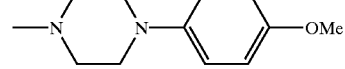 | 466 |
| 234 |  |  | 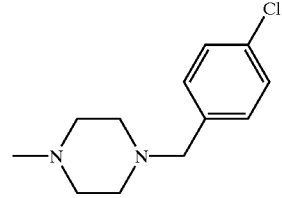 | 484 |
| 235 |  |  | 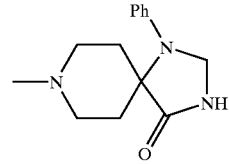 | 505 |
| 236 |  |  | 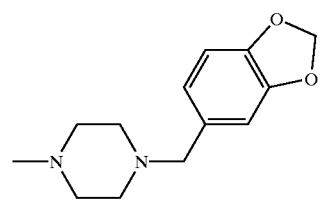 | 494 |
| 237 |  NHSO₂CH₃ |  |  | 444 |

TABLE 3-continued

Compounds of Formula (I)

| Compound No. | —R¹ | —A— | —N(R²)(R³) | [M + H]⁺ |
|---|---|---|---|---|
| 238 | CH₂CH₂CH₂NHSO₂CH₃ | –CH₂CH₂CH₂– | 4-[(4-chlorophenyl)(phenyl)methyl]piperazin-1-yl | 568 |
| 239 | CH₂CH₂CH₂NHSO₂CH₃ | –CH₂CH₂CH₂– | 4-benzylpiperazin-1-yl | 458 |
| 240 | CH₂CH₂CH₂NHSO₂CH₃ | –CH₂CH₂CH₂– | 4-(pyridin-2-yl)piperazin-1-yl | 445 |
| 241 | CH₂CH₂CH₂NHSO₂CH₃ | –CH₂CH₂CH₂– | 4-(3-chlorophenyl)piperazin-1-yl | 478 |
| 242 | CH₂CH₂CH₂NHSO₂CH₃ | –CH₂CH₂CH₂– | 4-(pyrimidin-2-yl)piperazin-1-yl | 446 |
| 243 | CH₂CH₂CH₂NHSO₂CH₃ | –CH₂CH₂CH₂– | 2,3,4,9-tetrahydro-1H-β-carbolin-2-yl | 454 |
| 244 | CH₂CH₂CH₂NHSO₂CH₃ | –CH₂CH₂CH₂– | 4-(3,5-dichloropyridin-4-yl)piperazin-1-yl | 513 |
| 245 | CH₂CH₂CH₂NHSO₂CH₃ | –CH₂CH₂CH₂– | 4-[3-(trifluoromethyl)phenyl]piperazin-1-yl | 512 |

TABLE 3-continued

Compounds of Formula (I)

| Compound No. | —R¹ | —A— | —N(R²)R³ | [M + H]⁺ |
|---|---|---|---|---|
| 246 | ~~NHSO₂CH₃ | ~~ | N-methylpiperidinyl-phenyl (tetrahydropyridine with phenyl) | 441 |
| 247 | ~~NHSO₂CH₃ | ~~ | N-methylpiperazinyl-(3,4-dichlorophenyl) | 512 |
| 248 | ~~NHSO₂CH₃ | ~~ | N-methylpiperidinyl-(benzimidazol-2-one) | 499 |
| 249 | ~~NHSO₂CH₃ | ~~ | N-methyl-4-hydroxypiperidinyl-(3-CF₃-4-Cl-phenyl) | 561 |
| 250 | ~~NHSO₂CH₃ | ~~ | N-methylpiperazinyl-(4-methoxyphenyl) | 474 |
| 251 | ~~NHSO₂CH₃ | ~~ | N-methylpiperazinyl-(4-chlorobenzyl) | 492 |
| 252 | ~~NHSO₂CH₃ | ~~ | N-methyl-1-phenyl-1,3,8-triazaspiro[4.5]decan-4-one | 513 |

TABLE 3-continued

Compounds of Formula (I)

| Compound No. | —R¹ | —A— | —N(R²)(R³) | [M + H]⁺ |
|---|---|---|---|---|
| 253 | propyl-NHSO₂CH₃ | propylene | piperazinyl-CH₂-benzo[1,3]dioxol-5-yl | 502 |
| 254 | propyl-NHSO₂CH₃ | propylene | piperazinyl-(2,3-dimethylphenyl) | 472 |
| 255 | propyl-NHSO₂CH₃ | propylene | piperazinyl-(2-methoxyphenyl) | 474 |
| 256 | propyl-NHSO₂CH₃ | propylene | piperazinyl-(3-methylphenyl) | 458 |
| 257 | propyl-NHSO₂CH₃ | propylene | piperazinyl-(2-methylphenyl) | 458 |
| 258 | propyl-NHSO₂CH₃ | propylene | piperazinyl-(2-chlorophenyl) | 478 |
| 259 | propyl-morpholino | cis-butenylene | piperazinyl-Ph | 462 |
| 260 | propyl-morpholino | cis-butenylene | piperazinyl-CH(Ph)(4-chlorophenyl) | 586 |

TABLE 3-continued
Compounds of Formula (I)
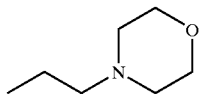
(I)
| Compound No. | —R¹ | —A— | —N(R²)(R³) | [M + H]⁺ |
|---|---|---|---|---|
| 261 | 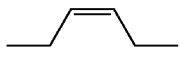 | 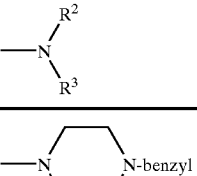 | 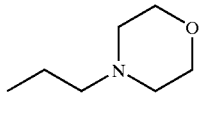 | 476 |
| 262 |  | 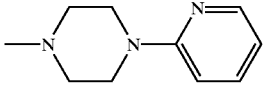 | 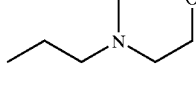 | 463 |
| 263 |  | 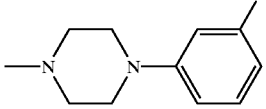 | 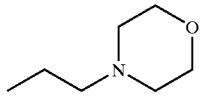 | 496 |
| 264 |  | 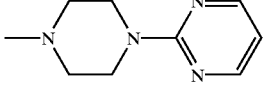 | 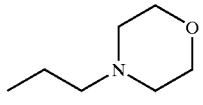 | 464 |
| 265 |  | 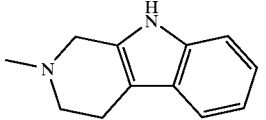 | 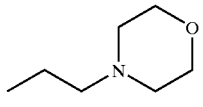 | 472 |
| 266 |  | 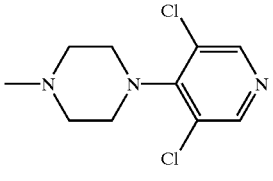 | 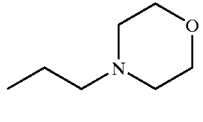 | 531 |
| 267 |  | 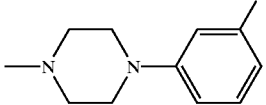 | 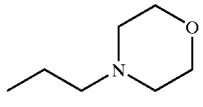 | 530 |
| 268 |  | 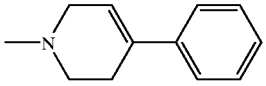 | 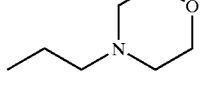 | 459 |
| 269 |  | 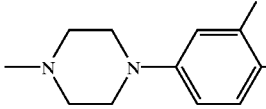 | | 530 |

US 6,521,623 B1
TABLE 3-continued
Compounds of Formula (I)
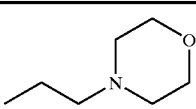
| Compound No. | —R¹ | —A— | —N(R²)(R³) | [M + H]⁺ |
|---|---|---|---|---|
| 270 | 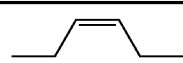 | 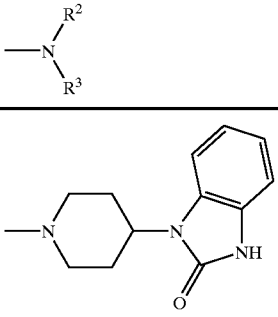 | 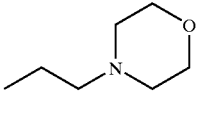 | 517 |
| 271 |  | 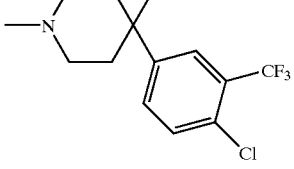 | 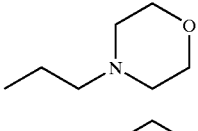 | 579 |
| 272 |  | 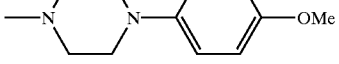 | 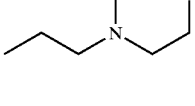 | 492 |
| 273 |  | 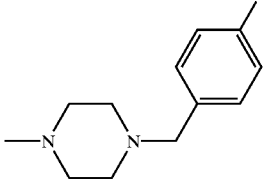 | 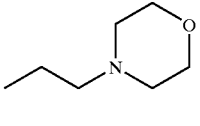 | 510 |
| 274 |  | 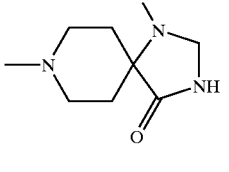 | 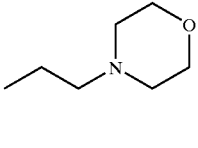 | 531 |
| 275 |  | 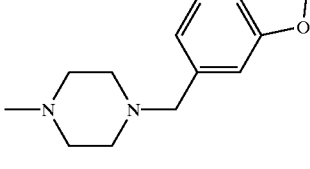 |  | 520 |
| 276 |  | 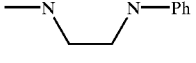 |  | 407 |

TABLE 3-continued

Compounds of Formula (I)

| Compound No. | —R¹ | —A— | —N(R²)(R³) | [M + H]⁺ |
|---|---|---|---|---|
| 277 | CH₂CH₂CH₂OMe | -CH₂-CH=CH-CH₂- (cis) | piperazine-N-CH(Ph)(4-chlorophenyl) | 531 |
| 278 | CH₂CH₂CH₂OMe | -CH₂-CH=CH-CH₂- (cis) | 4-benzylpiperazin-1-yl | 421 |
| 279 | CH₂CH₂CH₂OMe | -CH₂-CH=CH-CH₂- (cis) | 4-(pyridin-2-yl)piperazin-1-yl | 408 |
| 280 | CH₂CH₂CH₂OMe | -CH₂-CH=CH-CH₂- (cis) | 4-(3-chlorophenyl)piperazin-1-yl | 441 |
| 281 | CH₂CH₂CH₂OMe | -CH₂-CH=CH-CH₂- (cis) | 4-(pyrimidin-2-yl)piperazin-1-yl | 409 |
| 282 | CH₂CH₂CH₂OMe | -CH₂-CH=CH-CH₂- (cis) | 2,3,4,9-tetrahydro-1H-β-carbolin-2-yl | 417 |
| 283 | CH₂CH₂CH₂OMe | -CH₂-CH=CH-CH₂- (cis) | 4-(3,5-dichloropyridin-4-yl)piperazin-1-yl | 476 |
| 284 | CH₂CH₂CH₂OMe | -CH₂-CH=CH-CH₂- (cis) | 4-(3-trifluoromethylphenyl)piperazin-1-yl | 475 |

TABLE 3-continued

Compounds of Formula (I)

| Compound No. | —R¹ | —A— | —N(R²)(R³) | [M + H]⁺ |
|---|---|---|---|---|
| 285 | CH₂CH₂CH₂OMe | –CH₂–CH=CH–CH₂– (cis) | 4-phenyl-1,2,3,6-tetrahydropyridin-1-yl | 404 |
| 286 | CH₂CH₂CH₂OMe | –CH₂–CH=CH–CH₂– (cis) | 4-(3,4-dichlorophenyl)piperazin-1-yl | 475 |
| 287 | CH₂CH₂CH₂OMe | –CH₂–CH=CH–CH₂– (cis) | 1-(1-methylpiperidin-4-yl)-2,3-dihydro-1H-benzimidazol-2(3H)-one (linked via piperidine N) | 462 |
| 288 | CH₂CH₂CH₂OMe | –CH₂–CH=CH–CH₂– (cis) | 4-hydroxy-4-(4-chloro-3-trifluoromethylphenyl)piperidin-1-yl | 524 |
| 289 | CH₂CH₂CH₂OMe | –CH₂–CH=CH–CH₂– (cis) | 4-(4-methoxyphenyl)piperazin-1-yl | 437 |
| 290 | CH₂CH₂CH₂OMe | –CH₂–CH=CH–CH₂– (cis) | 4-(4-chlorobenzyl)piperazin-1-yl | 455 |
| 291 | CH₂CH₂CH₂OMe | –CH₂–CH=CH–CH₂– (cis) | 1-phenyl-4-oxo-1,3,8-triazaspiro[4.5]decan-8-yl | 476 |

TABLE 3-continued

Compounds of Formula (I)

| Compound No. | —R¹ | —A— | —N(R²)(R³) | [M + H]⁺ |
|---|---|---|---|---|
| 292 | propyl-OMe | cis-pentenyl | 4-(1,3-benzodioxol-5-ylmethyl)piperazin-1-yl | 465 |
| 293 | propyl-OMe | trans-pentenyl | 4-phenylpiperazin-1-yl | 407 |
| 294 | propyl-OMe | trans-pentenyl | 4-[(4-chlorophenyl)(phenyl)methyl]piperazin-1-yl | 531 |
| 295 | propyl-OMe | trans-pentenyl | 4-benzylpiperazin-1-yl | 421 |
| 296 | propyl-OMe | trans-pentenyl | 4-(pyridin-2-yl)piperazin-1-yl | 408 |
| 297 | propyl-OMe | trans-pentenyl | 4-(3-chlorophenyl)piperazin-1-yl | 441 |
| 298 | propyl-OMe | trans-pentenyl | 4-(pyrimidin-2-yl)piperazin-1-yl | 409 |
| 299 | propyl-OMe | trans-pentenyl | 2-methyl-2,3,4,9-tetrahydro-1H-β-carbolin-2-yl | 417 |

TABLE 3-continued

Compounds of Formula (I)

| Compound No. | —R¹ | —A— | —N(R²)(R³) | [M + H]⁺ |
|---|---|---|---|---|
| 300 | CH₂CH₂CH₂OMe | CH₂CH=CHCH₂ | 4-(3,5-dichloropyridin-4-yl)piperazin-1-yl | 432 |
| 301 | CH₂CH₂CH₂OMe | CH₂CH=CHCH₂ | 4-(3-trifluoromethylphenyl)piperazin-1-yl | 475 |
| 302 | CH₂CH₂CH₂OMe | CH₂CH=CHCH₂ | 4-phenyl-1,2,3,6-tetrahydropyridin-1-yl | 404 |
| 303 | CH₂CH₂CH₂OMe | CH₂CH=CHCH₂ | 4-(3,4-dichlorophenyl)piperazin-1-yl | 475 |
| 304 | CH₂CH₂CH₂OMe | CH₂CH=CHCH₂ | 4-(2-oxo-2,3-dihydro-1H-benzimidazol-1-yl)piperidin-1-yl | 462 |
| 305 | CH₂CH₂CH₂OMe | CH₂CH=CHCH₂ | 4-(4-chloro-3-trifluoromethylphenyl)-4-hydroxypiperidin-1-yl | 524 |
| 306 | CH₂CH₂CH₂OMe | CH₂CH=CHCH₂ | 4-(4-methoxyphenyl)piperazin-1-yl | 437 |

TABLE 3-continued

Compounds of Formula (I)

| Compound No. | —R¹ | —A— | —N(R²)(R³) | [M + H]⁺ |
|---|---|---|---|---|
| 307 | CH₂CH₂CH₂OMe | —CH₂CH=CHCH₂— | 4-(4-chlorobenzyl)piperazin-1-yl | 455 |
| 308 | CH₂CH₂CH₂OMe | —CH₂CH=CHCH₂— | 1-phenyl-8-methyl-4-oxo-1,3,8-triazaspiro[4.5]dec-3-yl | 476 |
| 309 | CH₂CH₂CH₂OMe | —CH₂CH=CHCH₂— | 4-(1,3-benzodioxol-5-ylmethyl)piperazin-1-yl | 465 |
| 310 | CH₂CH₂-(piperidin-1-yl) | —CH₂CH=CHCH₂— | 4-phenylpiperazin-1-yl | 460 |
| 311 | CH₂CH₂-(piperidin-1-yl) | —CH₂CH=CHCH₂— | 4-[(4-chlorophenyl)(phenyl)methyl]piperazin-1-yl | 584 |
| 312 | CH₂CH₂-(piperidin-1-yl) | —CH₂CH=CHCH₂— | 4-benzylpiperazin-1-yl | 474 |
| 313 | CH₂CH₂-(piperidin-1-yl) | —CH₂CH=CHCH₂— | 4-(pyridin-2-yl)piperazin-1-yl | 461 |

TABLE 3-continued
Compounds of Formula (I)
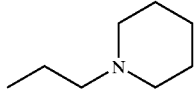
(I)
| Compound No. | —R¹ | —A— | —N(R²)(R³) | [M + H]⁺ |
|---|---|---|---|---|
| 314 | 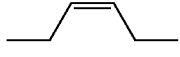 | 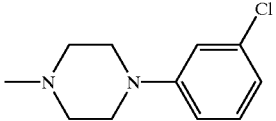 | 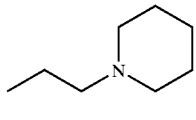 | 694 |
| 315 |  | 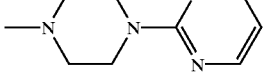 | 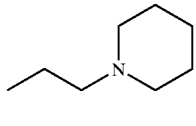 | 462 |
| 316 |  | 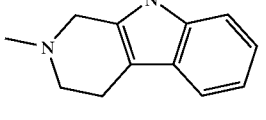 | 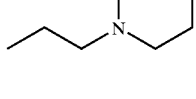 | 470 |
| 317 |  | 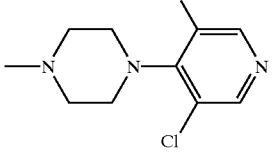 | 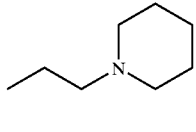 | 465 |
| 318 |  | 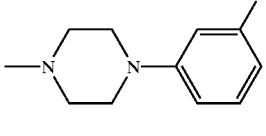 | 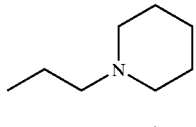 | 528 |
| 319 |  | 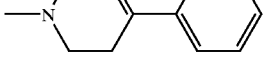 | 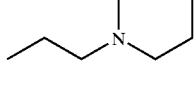 | 457 |
| 320 |  | 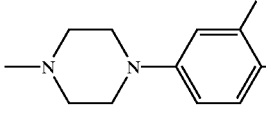 | 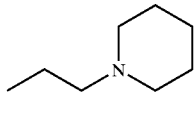 | 528 |
| 321 |  | 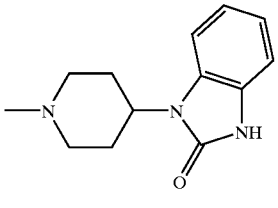 | | 515 |

TABLE 3-continued
Compounds of Formula (I)
| Compound No. | —R¹ | —A— | —N(R²)(R³) | [M + H]⁺ |
|---|---|---|---|---|
| 322 | 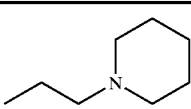 |  | 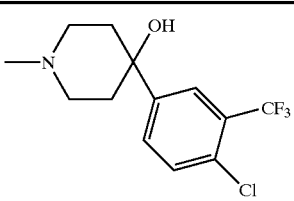 | 577 |
| 323 | 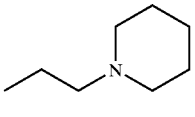 |  | 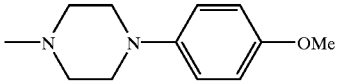 | 490 |
| 324 | 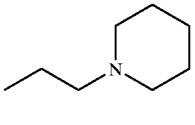 |  | 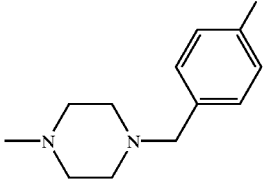 | 508 |
| 325 | 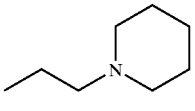 | 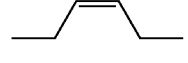 | 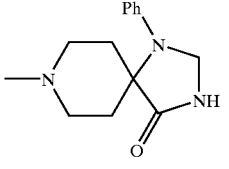 | 529 |
| 326 | 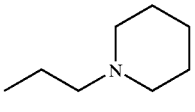 | 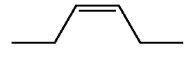 | 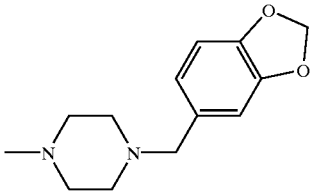 | 518 |
| 327 | 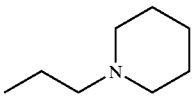 | 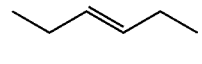 | 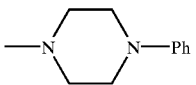 | 460 |
| 328 | 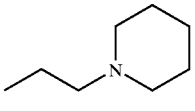 | 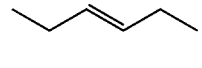 | 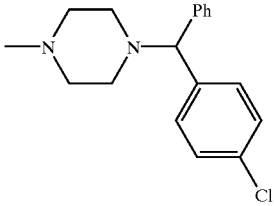 | 584 |

TABLE 3-continued
Compounds of Formula (I)
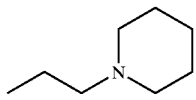
(I)
| Compound No. | —R¹ | —A— | —N(R²)(R³) | [M + H]⁺ |
|---|---|---|---|---|
| 329 | 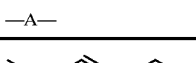 | 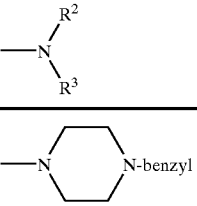 | 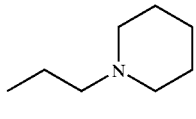 N-benzyl | 474 |
| 330 | 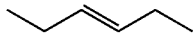 | 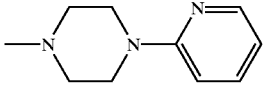 | 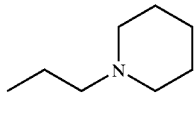 | 461 |
| 331 | 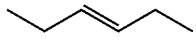 | 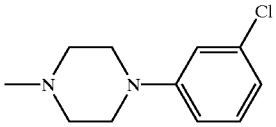 | 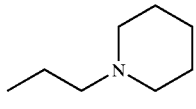 | 494 |
| 332 | 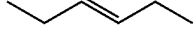 | 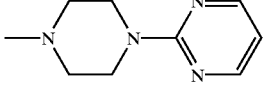 | 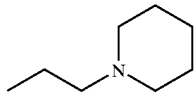 | 462 |
| 333 | 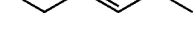 | 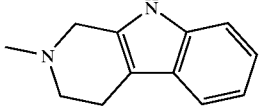 | 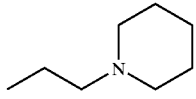 | 470 |
| 334 | 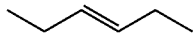 | 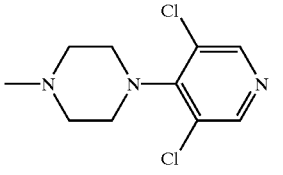 | 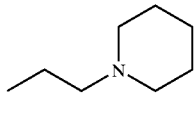 | 465 |
| 335 | 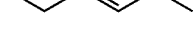 | 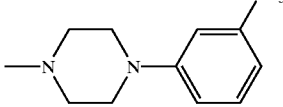 | 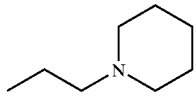 | 528 |
| 336 | 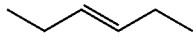 | 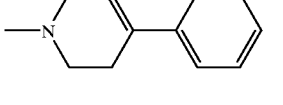 | 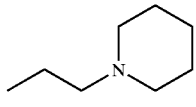 | 457 |
| 337 | 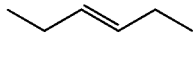 | 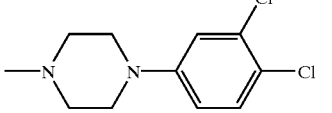 | | 528 |

US 6,521,623 B1
TABLE 3-continued
Compounds of Formula (I)
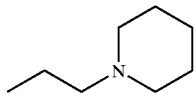
(I)
| Compound No. | —R¹ | —A— | —N(R²)(R³) | [M + H]⁺ |
|---|---|---|---|---|
| 338 | 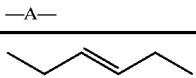 | 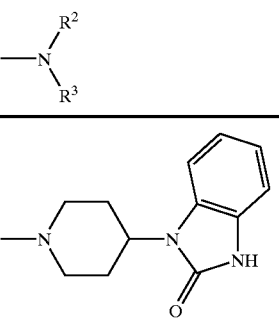 | 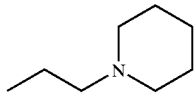 | 515 |
| 339 | 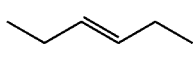 | 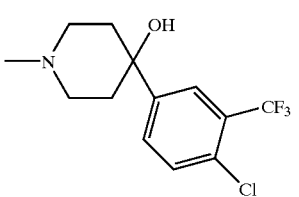 | 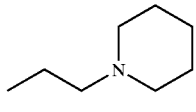 | 577 |
| 340 | 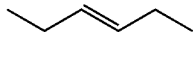 | 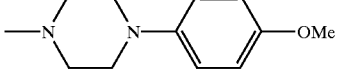 | 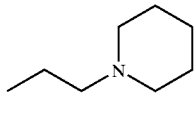 | 490 |
| 341 | 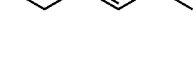 | 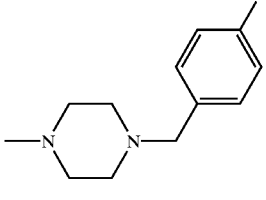 | 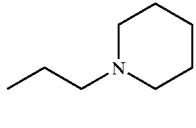 | 508 |
| 342 |  | 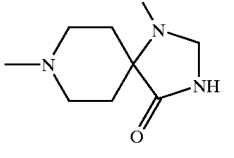 | 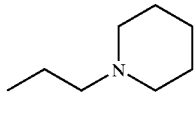 | 529 |
| 343 | 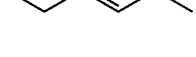 | 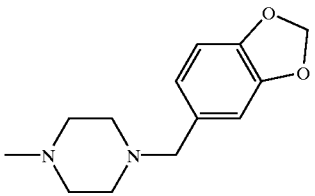 | 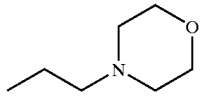 | 518 |
| 344 | 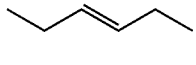 | 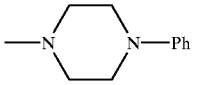 | —N⟨piperazine⟩—Ph | 462 |

TABLE 3-continued

Compounds of Formula (I)

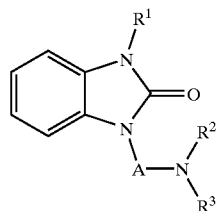

(I)

| Compound No. | —R¹ | —A— | —N(R²)(R³) | [M + H]⁺ |
|---|---|---|---|---|
| 345 | propyl-morpholine | -CH₂-CH=CH-CH₂- | piperazine-CH(Ph)(4-Cl-C₆H₄) | 586 |
| 346 | propyl-morpholine | -CH₂-CH=CH-CH₂- | piperazine-N-benzyl | 476 |
| 347 | propyl-morpholine | -CH₂-CH=CH-CH₂- | piperazine-(2-pyridyl) | 463 |
| 348 | propyl-morpholine | -CH₂-CH=CH-CH₂- | piperazine-(3-Cl-phenyl) | 496 |
| 349 | propyl-morpholine | -CH₂-CH=CH-CH₂- | piperazine-(2-pyrimidinyl) | 464 |
| 350 | propyl-morpholine | -CH₂-CH=CH-CH₂- | tetrahydro-β-carboline | 472 |
| 351 | propyl-morpholine | -CH₂-CH=CH-CH₂- | piperazine-(3,5-dichloro-4-pyridyl) | 467 |
| 352 | propyl-morpholine | -CH₂-CH=CH-CH₂- | piperazine-(3-CF₃-phenyl) | 530 |

TABLE 3-continued

Compounds of Formula (I)

| Compound No. | —R¹ | —A— | —N(R²)(R³) | [M + H]⁺ |
|---|---|---|---|---|
| 353 | propyl-morpholine | CH₂CH=CHCH₂ | 4-phenyl-1,2,3,6-tetrahydropyridin-1-yl | 459 |
| 354 | propyl-morpholine | CH₂CH=CHCH₂ | 4-(3,4-dichlorophenyl)piperazin-1-yl | 530 |
| 355 | propyl-morpholine | CH₂CH=CHCH₂ | 4-(2-oxo-2,3-dihydro-1H-benzimidazol-1-yl)piperidin-1-yl | 517 |
| 356 | propyl-morpholine | CH₂CH=CHCH₂ | 4-(4-chloro-3-trifluoromethylphenyl)-4-hydroxypiperidin-1-yl | 579 |
| 357 | propyl-morpholine | CH₂CH=CHCH₂ | 4-(4-methoxyphenyl)piperazin-1-yl | 492 |
| 358 | propyl-morpholine | CH₂CH=CHCH₂ | 4-(4-chlorobenzyl)piperazin-1-yl | 510 |
| 359 | propyl-morpholine | CH₂CH=CHCH₂ | 1-phenyl-4-oxo-1,3,8-triazaspiro[4.5]dec-8-yl | 531 |

TABLE 3-continued
Compounds of Formula (I)
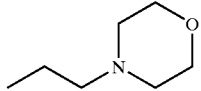
(I)
| Compound No. | —R¹ | —A— | —N(R²)(R³) | [M + H]⁺ |
|---|---|---|---|---|
| 360 | 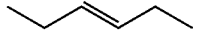 | 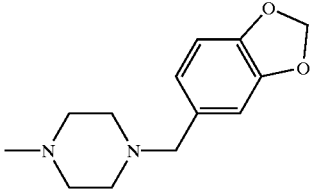 |  | 520 |
| 361 |  |  |  | 393 |
| 362 |  |  |  | 517 |
| 363 |  |  | 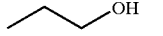 | 407 |
| 364 |  | 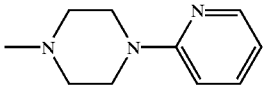 |  | 394 |
| 365 |  | 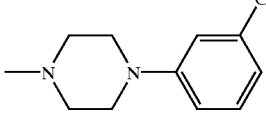 | 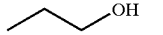 | 427 |
| 366 |  | 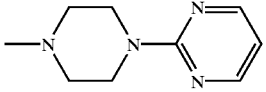 |  | 395 |
| 367 |  | 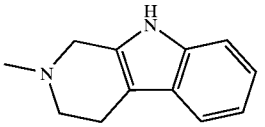 | | 403 |

TABLE 3-continued

Compounds of Formula (I)

| Compound No. | —R¹ | —A— | —N(R²)(R³) | [M + H]⁺ |
|---|---|---|---|---|
| 368 | propyl-OH | cis-CH₂CH=CHCH₂ | 4-(3,5-dichloropyridin-4-yl)piperazin-1-yl | 476 |
| 369 | propyl-OH | cis-CH₂CH=CHCH₂ | 4-(3-trifluoromethylphenyl)piperazin-1-yl | 461 |
| 370 | propyl-OH | cis-CH₂CH=CHCH₂ | 4-phenyl-3,6-dihydro-2H-pyridin-1-yl | 390 |
| 371 | propyl-OH | cis-CH₂CH=CHCH₂ | 4-(3,4-dichlorophenyl)piperazin-1-yl | 461 |
| 372 | propyl-OH | cis-CH₂CH=CHCH₂ | 4-(2-oxo-2,3-dihydro-1H-benzimidazol-1-yl)piperidin-1-yl | 448 |
| 373 | propyl-OH | cis-CH₂CH=CHCH₂ | 4-hydroxy-4-(4-chloro-3-trifluoromethylphenyl)piperidin-1-yl | 510 |
| 374 | propyl-OH | cis-CH₂CH=CHCH₂ | 4-(4-methoxyphenyl)piperazin-1-yl | 423 |

TABLE 3-continued

Compounds of Formula (I)

| Compound No. | —R¹ | —A— | —N(R²)(R³) | [M + H]⁺ |
|---|---|---|---|---|
| 375 | propyl-OH | cis-CH₂CH=CHCH₂ | 4-(4-chlorobenzyl)piperazin-1-yl | 441 |
| 376 | propyl-OH | cis-CH₂CH=CHCH₂ | 1-phenyl-8-methyl-4-oxo-1,3,8-triazaspiro[4.5]decan-3-yl | 462 |
| 377 | propyl-OH | cis-CH₂CH=CHCH₂ | 4-(1,3-benzodioxol-5-ylmethyl)piperazin-1-yl | 451 |
| 378 | propyl-OH | trans-CH₂CH=CHCH₂ | 4-phenylpiperazin-1-yl | 393 |
| 379 | propyl-OH | trans-CH₂CH=CHCH₂ | 4-[(4-chlorophenyl)(phenyl)methyl]piperazin-1-yl | 517 |
| 380 | propyl-OH | trans-CH₂CH=CHCH₂ | 4-benzylpiperazin-1-yl | 407 |
| 381 | propyl-OH | trans-CH₂CH=CHCH₂ | 4-(pyridin-2-yl)piperazin-1-yl | 394 |

TABLE 3-continued

Compounds of Formula (I)

| Compound No. | —R¹ | —A— | —N(R²)R³ | [M + H]⁺ |
|---|---|---|---|---|
| 382 | propyl-OH | -CH₂-CH=CH-CH₂- | 4-(3-chlorophenyl)piperazin-1-yl | 427 |
| 383 | propyl-OH | -CH₂-CH=CH-CH₂- | 4-(pyrimidin-2-yl)piperazin-1-yl | 395 |
| 384 | propyl-OH | -CH₂-CH=CH-CH₂- | 1,2,3,4-tetrahydro-β-carbolin-2-yl | 403 |
| 385 | propyl-OH | -CH₂-CH=CH-CH₂- | 4-(3,5-dichloropyridin-4-yl)piperazin-1-yl | 476 |
| 386 | propyl-OH | -CH₂-CH=CH-CH₂- | 4-(3-trifluoromethylphenyl)piperazin-1-yl | 461 |
| 387 | propyl-OH | -CH₂-CH=CH-CH₂- | 4-phenyl-1,2,3,6-tetrahydropyridin-1-yl | 390 |
| 388 | propyl-OH | -CH₂-CH=CH-CH₂- | 4-(3,4-dichlorophenyl)piperazin-1-yl | 461 |
| 389 | propyl-OH | -CH₂-CH=CH-CH₂- | 4-(2-oxo-2,3-dihydro-1H-benzimidazol-1-yl)piperidin-1-yl | 448 |

TABLE 3-continued

Compounds of Formula (I)

| Compound No. | —R¹ | —A— | —N(R²)(R³) | [M + H]⁺ |
|---|---|---|---|---|
| 390 | propyl-OH | -CH=CH-CH₂- (trans) | N-methylpiperidine-4-ol with 4-Cl-3-CF₃-phenyl | 510 |
| 391 | propyl-OH | -CH=CH-CH₂- (trans) | 4-(4-methoxyphenyl)piperazin-1-yl | 423 |
| 392 | propyl-OH | -CH=CH-CH₂- (trans) | 4-(4-chlorobenzyl)piperazin-1-yl | 441 |
| 393 | propyl-OH | -CH=CH-CH₂- (trans) | 1-phenyl-1,3,8-triazaspiro[4.5]decan-4-one-8-yl | 462 |
| 394 | propyl-OH | -CH=CH-CH₂- (trans) | 4-(benzo[1,3]dioxol-5-ylmethyl)piperazin-1-yl | 451 |
| 395 | propyl-O-C(=O)-NHEthyl | -CH=CH-CH₂- (cis) | 4-phenylpiperazin-1-yl | 464 |
| 396 | propyl-O-C(=O)-NHEthyl | -CH=CH-CH₂- (cis) | 4-[(4-chlorophenyl)(phenyl)methyl]piperazin-1-yl | 588 |

TABLE 3-continued

Compounds of Formula (I)

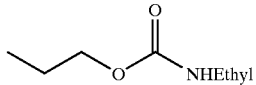

| Compound No. | —R¹ | —A— | —N(R²)(R³) | [M + H]⁺ |
|---|---|---|---|---|
| 397 | propyl-O-C(O)-NHEthyl | -CH₂CH=CHCH₂- | piperazine-N-benzyl | 478 |
| 398 | propyl-O-C(O)-NHEthyl | -CH₂CH=CHCH₂- | piperazine-2-pyridyl | 465 |
| 399 | propyl-O-C(O)-NHEthyl | -CH₂CH=CHCH₂- | piperazine-(3-Cl-phenyl) | 699 |
| 400 | propyl-O-C(O)-NHEthyl | -CH₂CH=CHCH₂- | piperazine-2-pyrimidinyl | 466 |
| 401 | propyl-O-C(O)-NHEthyl | -CH₂CH=CHCH₂- | tetrahydro-β-carboline | 474 |
| 402 | propyl-O-C(O)-NHEthyl | -CH₂CH=CHCH₂- | piperazine-(3,5-diCl-4-pyridyl) | 469 |
| 403 | propyl-O-C(O)-NHEthyl | -CH₂CH=CHCH₂- | piperazine-(3-CF₃-phenyl) | 532 |
| 404 | propyl-O-C(O)-NHEthyl | -CH₂CH=CHCH₂- | 4-phenyl-tetrahydropyridine | 461 |
| 405 | propyl-O-C(O)-NHEthyl | -CH₂CH=CHCH₂- | piperazine-(3,4-diCl-phenyl) | 532 |

TABLE 3-continued

Compounds of Formula (I)

| Compound No. | —R¹ | —A— | —N(R²)R³ | [M + H]⁺ |
|---|---|---|---|---|
| 406 | propyl-O-C(O)-NHEthyl | cis-CH₂CH=CHCH₂ | 4-(2-oxo-2,3-dihydro-1H-benzimidazol-1-yl)piperidin-1-yl | 519 |
| 407 | propyl-O-C(O)-NHEthyl | cis-CH₂CH=CHCH₂ | 4-hydroxy-4-(4-chloro-3-trifluoromethylphenyl)piperidin-1-yl | 581 |
| 408 | propyl-O-C(O)-NHEthyl | cis-CH₂CH=CHCH₂ | 4-(4-methoxyphenyl)piperazin-1-yl | 494 |
| 409 | propyl-O-C(O)-NHEthyl | cis-CH₂CH=CHCH₂ | 4-(4-chlorobenzyl)piperazin-1-yl | 512 |
| 410 | propyl-O-C(O)-NHEthyl | cis-CH₂CH=CHCH₂ | 1-phenyl-1,3,8-triazaspiro[4.5]decan-4-on-8-yl | 533 |
| 411 | propyl-O-C(O)-NHEthyl | cis-CH₂CH=CHCH₂ | 4-(benzo[1,3]dioxol-5-ylmethyl)piperazin-1-yl | 522 |
| 412 | propyl-O-C(O)-NHEthyl | trans-CH₂CH=CHCH₂ | 4-phenylpiperazin-1-yl | 464 |

TABLE 3-continued

Compounds of Formula (I)

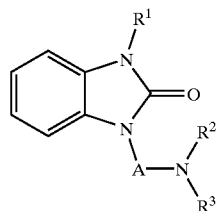

(I)

| Compound No. | —R¹ | —A— | —N(R²)(R³) | [M + H]⁺ |
|---|---|---|---|---|
| 413 | propyl-O-C(O)-NHEthyl | -CH2-CH=CH-CH2- | piperazine-CH(Ph)(4-Cl-C6H4) | 588 |
| 414 | propyl-O-C(O)-NHEthyl | -CH2-CH=CH-CH2- | piperazine-N-benzyl | 478 |
| 415 | propyl-O-C(O)-NHEthyl | -CH2-CH=CH-CH2- | piperazine-(2-pyridyl) | 465 |
| 416 | propyl-O-C(O)-NHEthyl | -CH2-CH=CH-CH2- | piperazine-(3-Cl-C6H4) | 498 |
| 417 | propyl-O-C(O)-NHEthyl | -CH2-CH=CH-CH2- | piperazine-(2-pyrimidinyl) | 466 |
| 418 | propyl-O-C(O)-NHEthyl | -CH2-CH=CH-CH2- | tetrahydro-β-carboline | 474 |
| 419 | propyl-O-C(O)-NHEthyl | -CH2-CH=CH-CH2- | piperazine-(3,5-diCl-4-pyridyl) | 469 |
| 420 | propyl-O-C(O)-NHEthyl | -CH2-CH=CH-CH2- | piperazine-(3-CF3-C6H4) | 532 |

TABLE 3-continued

Compounds of Formula (I)

| Compound No. | —R¹ | —A— | —N(R²)(R³) | [M + H]⁺ |
|---|---|---|---|---|
| 421 | propyl O-C(=O)-NHEthyl | -CH2-CH=CH-CH2- | N-methyl-4-phenyl-1,2,3,6-tetrahydropyridin-1-yl | 461 |
| 422 | propyl O-C(=O)-NHEthyl | -CH2-CH=CH-CH2- | 4-(3,4-dichlorophenyl)piperazin-1-yl | 532 |
| 423 | propyl O-C(=O)-NHEthyl | -CH2-CH=CH-CH2- | 4-(2-oxo-2,3-dihydro-1H-benzimidazol-1-yl)piperidin-1-yl | 519 |
| 424 | propyl O-C(=O)-NHEthyl | -CH2-CH=CH-CH2- | 4-(4-chloro-3-trifluoromethylphenyl)-4-hydroxypiperidin-1-yl | 581 |
| 425 | propyl O-C(=O)-NHEthyl | -CH2-CH=CH-CH2- | 4-(4-methoxyphenyl)piperazin-1-yl | 494 |
| 426 | propyl O-C(=O)-NHEthyl | -CH2-CH=CH-CH2- | 4-(4-chlorobenzyl)piperazin-1-yl | 512 |
| 427 | propyl O-C(=O)-NHEthyl | -CH2-CH=CH-CH2- | 1-phenyl-4-oxo-1,3,8-triazaspiro[4.5]dec-8-yl | 533 |

TABLE 3-continued

Compounds of Formula (I)

| Compound No. | —R¹ | —A— | —N(R²)R³ | [M + H]⁺ |
|---|---|---|---|---|
| 428 | propyl-O-C(O)-NHEthyl | -CH₂-CH=CH-CH₂- | piperazinyl-CH₂-(benzo[1,3]dioxol-5-yl) | 522 |
| 429 | propyl-NH-C(O)-CH₃ | -(CH₂)₄- | piperazinyl-Ph | 408 |
| 430 | propyl-NH-C(O)-CH₃ | -(CH₂)₄- | piperazinyl-CH(Ph)(4-Cl-C₆H₄) | 532 |
| 431 | propyl-NH-C(O)-CH₃ | -(CH₂)₄- | piperazinyl-N-benzyl | 422 |
| 432 | propyl-NH-C(O)-CH₃ | -(CH₂)₄- | piperazinyl-(2-pyridyl) | 409 |
| 433 | propyl-NH-C(O)-CH₃ | -(CH₂)₄- | piperazinyl-(3-Cl-C₆H₄) | 442 |
| 434 | propyl-NH-C(O)-CH₃ | -(CH₂)₄- | piperazinyl-(2-pyrimidinyl) | 410 |
| 435 | propyl-NH-C(O)-CH₃ | -(CH₂)₄- | 2-methyl-1,2,3,4-tetrahydro-β-carbolin-2-yl | 418 |

TABLE 3-continued
Compounds of Formula (I)
| Compound No. | —R¹ | —A— | —N(R²)(R³) | [M + H]⁺ |
|---|---|---|---|---|
| 436 |  | 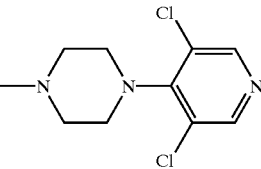 |  | 477 |
| 437 |  | 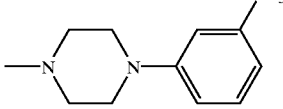 |  | 476 |
| 438 |  | 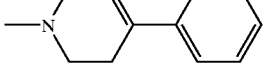 |  | 405 |
| 439 |  | 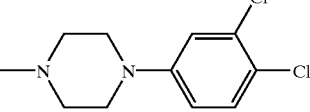 |  | 476 |
| 440 |  | 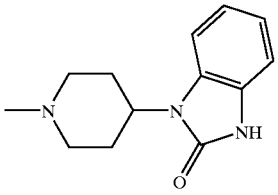 |  | 463 |
| 441 |  | 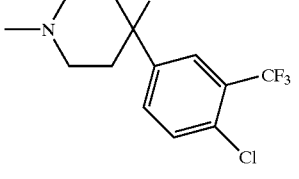 |  | 525 |
| 442 |  | 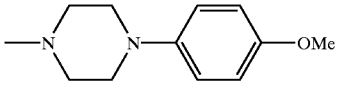 | | 438 |

TABLE 3-continued

Compounds of Formula (I)

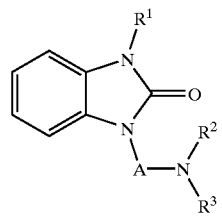

(I)

| Compound No. | —R¹ | —A— | —N(R²)(R³) | [M + H]⁺ |
|---|---|---|---|---|
| 443 | propyl-NH-C(O)-CH₃ | butylene | 4-(4-chlorobenzyl)piperazin-1-yl | 456 |
| 444 | propyl-NH-C(O)-CH₃ | butylene | 1-phenyl-4-methyl-1,3,8-triazaspiro[4.5]decan-4-one-8-yl | 477 |
| 445 | propyl-NH-C(O)-CH₃ | butylene | 4-(1,3-benzodioxol-5-ylmethyl)piperazin-1-yl | 466 |
| 446 | propyl-NH-C(O)-CH₃ | butylene | 4-(2,3-dimethylphenyl)piperazin-1-yl | 436 |
| 447 | propyl-NH-C(O)-CH₃ | butylene | 4-(2-methoxyphenyl)piperazin-1-yl | 438 |
| 448 | propyl-NH-C(O)-CH₃ | butylene | 4-(3-methylphenyl)piperazin-1-yl | 422 |
| 449 | propyl-NH-C(O)-CH₃ | butylene | 4-(2-methylphenyl)piperazin-1-yl | 422 |

TABLE 3-continued

Compounds of Formula (I)

| Compound No. | —R¹ | —A— | —N(R²)(R³) | [M + H]⁺ |
|---|---|---|---|---|
| 450 | propyl-NH-C(O)-CH₃ | butylene | piperazinyl-(2-Cl-phenyl) | 442 |
| 451 | propyl-NH-C(O)-CH₃ | cis-butenylene | piperazinyl-Ph | 434 |
| 452 | propyl-NH-C(O)-CH₃ | cis-butenylene | piperazinyl-CH(Ph)(4-Cl-phenyl) | 558 |
| 453 | propyl-NH-C(O)-CH₃ | cis-butenylene | piperazinyl-N-benzyl | 448 |
| 454 | propyl-NH-C(O)-CH₃ | cis-butenylene | piperazinyl-(2-pyridyl) | 435 |
| 455 | propyl-NH-C(O)-CH₃ | cis-butenylene | piperazinyl-(3-Cl-phenyl) | 468 |
| 456 | propyl-NH-C(O)-CH₃ | cis-butenylene | piperazinyl-(2-pyrimidyl) | 436 |
| 457 | propyl-NH-C(O)-CH₃ | cis-butenylene | tetrahydro-β-carbolin-2-yl | 444 |

TABLE 3-continued
Compounds of Formula (I)
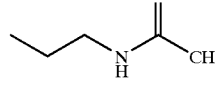
| Compound No. | —R¹ | —A— | —N(R²)(R³) | [M + H]⁺ |
|---|---|---|---|---|
| 458 |  | 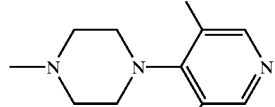 |  | 503 |
| 459 |  | 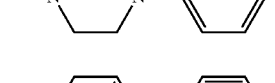 |  | 502 |
| 460 |  |  |  | 431 |
| 461 | 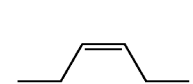 |  |  | 502 |
| 462 |  | 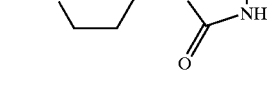 | 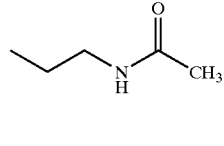 | 489 |
| 463 |  | 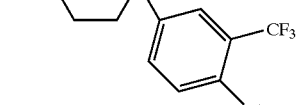 | 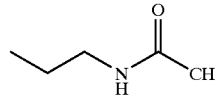 | 551 |
| 464 | 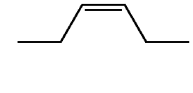 | | 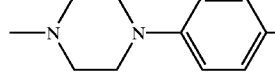 | 464 |

TABLE 3-continued
Compounds of Formula (I)
(I)
| Compound No. | —R¹ | —A— | −N(R²)(R³) | [M + H]⁺ |
|---|---|---|---|---|
| 465 |  | 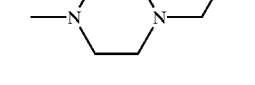 |  | 482 |
| 466 |  | 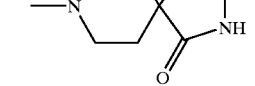 | 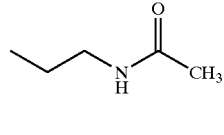 | 503 |
| 467 |  | 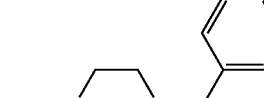 | 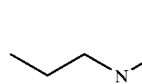 | 492 |
| 468 | 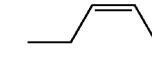 | 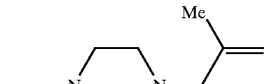 | 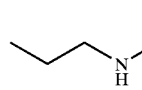 | 462 |
| 469 | 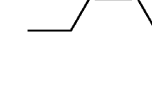 | 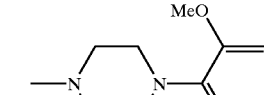 | 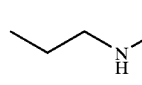 | 464 |
| 470 | 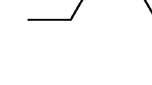 | 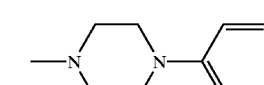 | 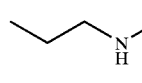 | 448 |
| 471 | 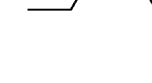 | 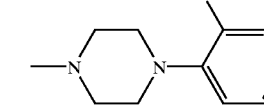 | | 448 |

TABLE 3-continued

Compounds of Formula (I)

| Compound No. | —R¹ | —A— | —N(R²)(R³) | [M + H]⁺ |
|---|---|---|---|---|
| 472 | propyl-NH-C(O)-CH₃ | -CH₂-CH=CH-CH₂- | piperazinyl-(2-chlorophenyl) | 468 |
| 473 | propyl-NH-C(O)-CH₃ | -CH₂-CH=CH-CH₂- | piperazinyl-Ph | 434 |
| 474 | propyl-NH-C(O)-CH₃ | -CH₂-CH=CH-CH₂- | piperazinyl-CH(Ph)(4-chlorophenyl) | 558 |
| 475 | propyl-NH-C(O)-CH₃ | -CH₂-CH=CH-CH₂- | piperazinyl-N-benzyl | 448 |
| 476 | propyl-NH-C(O)-CH₃ | -CH₂-CH=CH-CH₂- | piperazinyl-(2-pyridyl) | 435 |
| 477 | propyl-NH-C(O)-CH₃ | -CH₂-CH=CH-CH₂- | piperazinyl-(3-chlorophenyl) | 468 |
| 478 | propyl-NH-C(O)-CH₃ | -CH₂-CH=CH-CH₂- | piperazinyl-(2-pyrimidinyl) | 436 |
| 479 | propyl-NH-C(O)-CH₃ | -CH₂-CH=CH-CH₂- | tetrahydro-β-carbolin-2-yl | 444 |

TABLE 3-continued
Compounds of Formula (I)
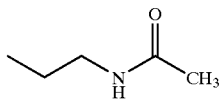
| Compound No. | —R¹ | —A— | —N(R²)(R³) | [M + H]⁺ |
|---|---|---|---|---|
| 480 | 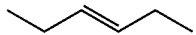 | 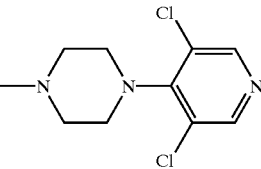 | 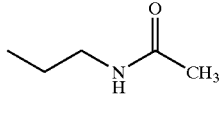 | 503 |
| 481 |  | 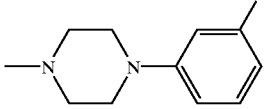 | 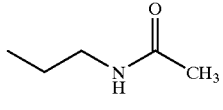 | 502 |
| 482 | 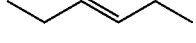 | 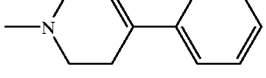 | 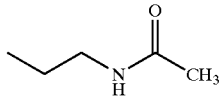 | 431 |
| 483 | 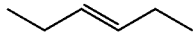 | 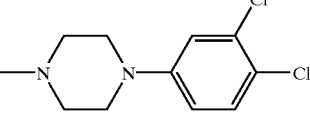 | 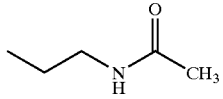 | 502 |
| 484 | 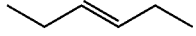 | 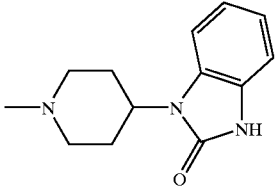 | 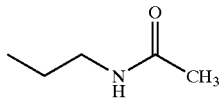 | 489 |
| 485 | 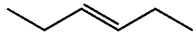 | 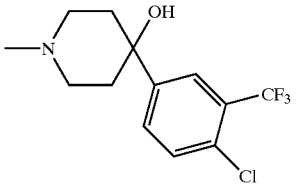 | 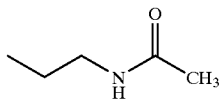 | 551 |
| 486 | 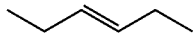 | 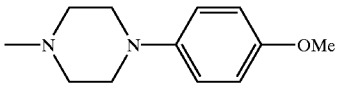 | | 464 |

TABLE 3-continued
Compounds of Formula (I)
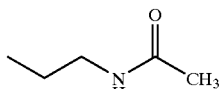
(I)
| Compound No. | —R¹ | —A— | $-N\begin{matrix}R^2\\R^3\end{matrix}$ | [M + H]⁺ |
|---|---|---|---|---|
| 487 | 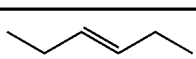 | 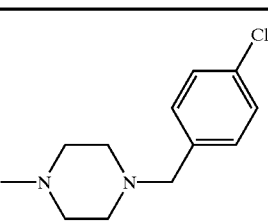 | 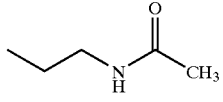 | 482 |
| 488 | 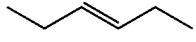 | 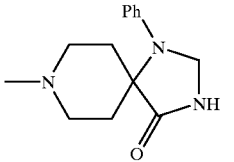 | 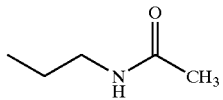 | 503 |
| 489 | 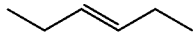 | 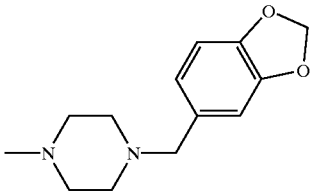 | 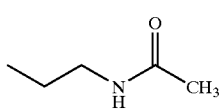 | 492 |
| 490 | 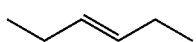 | 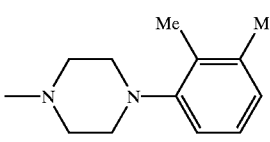 | 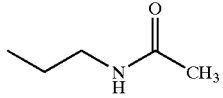 | 462 |
| 491 | 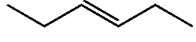 | 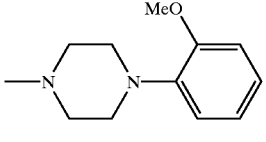 | 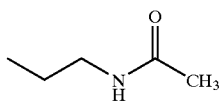 | 464 |
| 492 | 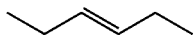 | 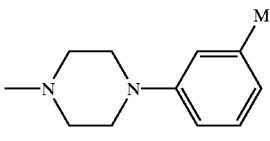 | 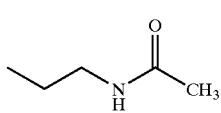 | 448 |
| 493 | 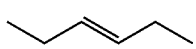 | 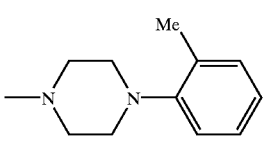 | | 448 |

TABLE 3-continued

Compounds of Formula (I)

| Compound No. | —R¹ | —A— | R³) | [M + H]⁺ |
|---|---|---|---|---|
| 494 | propyl-NHC(O)CH₃ | -CH₂-CH=CH-CH₂-CH₂- | 4-(2-chlorophenyl)piperazin-1-yl | 468 |
| 495 | propyl-NHSO₂CH₃ | -CH₂-CH=CH-CH₂- | 4-phenylpiperazin-1-yl | 470 |
| 496 | propyl-NHSO₂CH₃ | -CH₂-CH=CH-CH₂- | 4-[(4-chlorophenyl)(phenyl)methyl]piperazin-1-yl | 594 |
| 497 | propyl-NHSO₂CH₃ | -CH₂-CH=CH-CH₂- | 4-benzylpiperazin-1-yl | 484 |
| 498 | propyl-NHSO₂CH₃ | -CH₂-CH=CH-CH₂- | 4-(pyridin-2-yl)piperazin-1-yl | 471 |
| 499 | propyl-NHSO₂CH₃ | -CH₂-CH=CH-CH₂- | 4-(3-chlorophenyl)piperazin-1-yl | 504 |
| 500 | propyl-NHSO₂CH₃ | -CH₂-CH=CH-CH₂- | 4-(pyrimidin-2-yl)piperazin-1-yl | 472 |
| 501 | propyl-NHSO₂CH₃ | -CH₂-CH=CH-CH₂- | 2-methyl-2,3,4,9-tetrahydro-1H-β-carbolin-2-yl | 480 |

TABLE 3-continued
Compounds of Formula (I)
(I)
| Compound No. | —R¹ | —A— | $-N\begin{matrix}R^2\\R^3\end{matrix}$ | [M + H]⁺ |
|---|---|---|---|---|
| 502 |  | 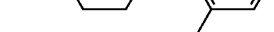 |  | 539 |
| 503 |  | 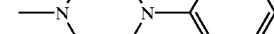 |  | 538 |
| 504 |  | 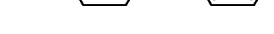 |  | 467 |
| 505 |  | 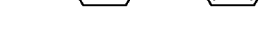 |  | 538 |
| 506 |  |  |  | 525 |
| 507 |  |  |  | 587 |
| 508 | 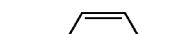 | 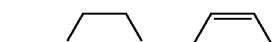 | | 500 |

TABLE 3-continued
Compounds of Formula (I)
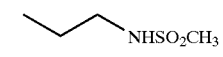
(I)
| Compound No. | —R¹ | —A— | —N(R²)(R³) | [M + H]⁺ |
|---|---|---|---|---|
| 509 | 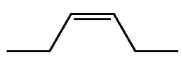 | 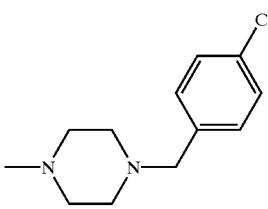 | 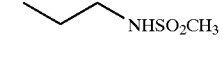 | 518 |
| 510 | 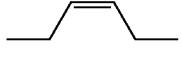 | 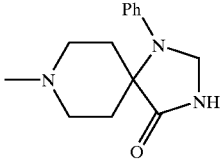 | 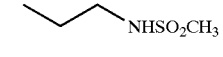 | 539 |
| 511 | 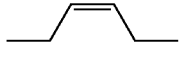 | 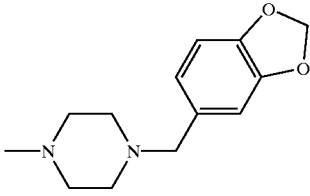 | 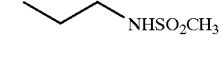 | 528 |
| 512 | 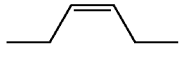 | 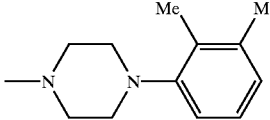 | 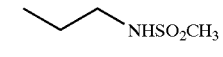 | 498 |
| 513 | 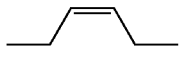 | 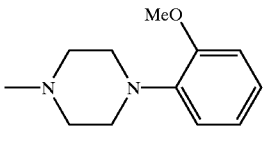 | 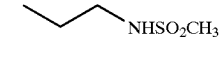 | 500 |
| 514 | 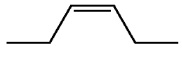 | 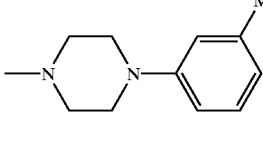 |  | 484 |
| 515 |  | 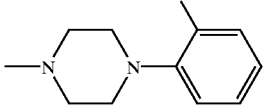 | | 484 |

TABLE 3-continued

Compounds of Formula (I)

| Compound No. | —R¹ | —A— | —N(R²)(R³) | [M + H]⁺ |
|---|---|---|---|---|
| 516 | ~NHSO₂CH₃ | cis-CH₂CH=CHCH₂ | piperazine-N-(2-chlorophenyl) | 504 |
| 517 | ~NHSO₂CH₃ | trans-CH₂CH=CHCH₂ | piperazine-N-Ph | 470 |
| 518 | ~NHSO₂CH₃ | trans-CH₂CH=CHCH₂ | piperazine-N-CH(Ph)(4-chlorophenyl) | 594 |
| 519 | ~NHSO₂CH₃ | trans-CH₂CH=CHCH₂ | piperazine-N-benzyl | 484 |
| 520 | ~NHSO₂CH₃ | trans-CH₂CH=CHCH₂ | piperazine-N-(2-pyridyl) | 471 |
| 521 | ~NHSO₂CH₃ | trans-CH₂CH=CHCH₂ | piperazine-N-(3-chlorophenyl) | 504 |
| 522 | ~NHSO₂CH₃ | trans-CH₂CH=CHCH₂ | piperazine-N-(2-pyrimidyl) | 472 |
| 523 | ~NHSO₂CH₃ | trans-CH₂CH=CHCH₂ | 2-methyl-1,2,3,4-tetrahydro-β-carbolin-2-yl | 480 |

TABLE 3-continued

Compounds of Formula (I)

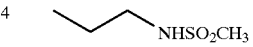

| Compound No. | —R¹ | —A— | —N(R²)(R³) | [M + H]⁺ |
|---|---|---|---|---|
| 524 | ~~~NHSO₂CH₃ | ~~~ | 3,5-dichloropyridin-4-yl piperazine | 539 |
| 525 | ~~~NHSO₂CH₃ | ~~~ | 3-(trifluoromethyl)phenyl piperazine | 538 |
| 526 | ~~~NHSO₂CH₃ | ~~~ | 4-phenyl-tetrahydropyridine | 467 |
| 527 | ~~~NHSO₂CH₃ | ~~~ | 3,4-dichlorophenyl piperazine | 538 |
| 528 | ~~~NHSO₂CH₃ | ~~~ | 1-(benzimidazol-2-on-1-yl)piperidine | 525 |
| 529 | ~~~NHSO₂CH₃ | ~~~ | 4-(4-chloro-3-trifluoromethylphenyl)-4-hydroxypiperidine | 587 |
| 530 | ~~~NHSO₂CH₃ | ~~~ | 4-methoxyphenyl piperazine | 500 |

US 6,521,623 B1

TABLE 3-continued

Compounds of Formula (I)

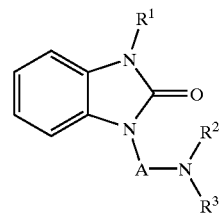

(I)

| Compound No. | —R¹ | —A— | —N(R²)(R³) | [M + H]⁺ |
|---|---|---|---|---|
| 531 | ∼∼NHSO₂CH₃ | ∼∼CH=CH∼ | N-methylpiperazine-CH₂-(4-chlorophenyl) | 518 |
| 532 | ∼∼NHSO₂CH₃ | ∼∼CH=CH∼ | 8-methyl-1-phenyl-1,3,8-triazaspiro[4.5]decan-4-one | 539 |
| 533 | ∼∼NHSO₂CH₃ | ∼∼CH=CH∼ | N-methylpiperazine-CH₂-(benzo[1,3]dioxol-5-yl) | 528 |
| 534 | ∼∼NHSO₂CH₃ | ∼∼CH=CH∼ | N-methylpiperazine-(2,3-dimethylphenyl) | 498 |
| 535 | ∼∼NHSO₂CH₃ | ∼∼CH=CH∼ | N-methylpiperazine-(2-methoxyphenyl) | 500 |
| 536 | ∼∼NHSO₂CH₃ | ∼∼CH=CH∼ | N-methylpiperazine-(3-methylphenyl) | 484 |
| 537 | ∼∼NHSO₂CH₃ | ∼∼CH=CH∼ | N-methylpiperazine-(2-methylphenyl) | 484 |

TABLE 3-continued

Compounds of Formula (I)

| Compound No. | —R¹ | —A— | $-N\overset{R^2}{\underset{R^3}{\diagdown}}$ | [M + H]⁺ |
|---|---|---|---|---|
| 538 | ~~NHSO₂CH₃ | ~~ (trans CH=CH) | piperazinyl-(2-chlorophenyl) | 504 |

The biological profile of the compounds of the invention, was assessed by evaluating their activity at the 5-HT$_{1A}$, 5-HT$_{2A}$, and D$_4$ receptors, according to the methods described below.

Receptor Binding Studies

Receptor binding studies were carried out to determine the affinity of the compounds for 5-HT$_{1A}$, 5-HT$_{2A}$, and D$_4$ receptors 5HT$_{1A}$ Radioligand Receptor Binding Assay Membranes from CHO cells, expressing 5-HT$_{1A}$ human receptors were suspended in incubation buffer.

Binding Assay:

Binding assays were performed in MultiProbe 204 pipetting system (Packard), according to a predetermined mapping, consistent with the software Screen. The compounds were tested in singlicate at one concentration ($10^{-7}$ M) in a total volume of 1000 μl. 980 μl of diluted membranes, 10 μl DMSO or unlabelled ligand and 10 μl of [$^3$H]-8-OH-DPAT (0.6–0.7 nM) were incubated for 60 minutes at 27° C. The reaction was stopped by rapid filtration through Tomtec Cell Harvester (48 wells) using Filtermat B (presoaked in 0.1% PEI) filters. Filters were washed with ice-cold 50 mM Tris-HCl (pH 7.4) buffer (9×700 μl), dried, covered with MeltiLex B/HS scintillator sheets (Wallac) and heated at 80° C. to 90° C. for about 10 minutes, transferred into plastic sample bags (Wallac), sealed, and put into 1024 Beta Plate scintillation counter (Wallac). Non-specific binding was determined in the presence of 5-HT ($10^{-5}$ M).

Data Analysis:

The specific radioligand binding to the receptor was defined by the difference between total binding and non-specific binding, determined in the presence of an excess of unlabelled ligand. Results were expressed as percentage of control specific binding obtained in the presence of the compounds. The affinity values (IC$_{50}$) for the compounds were obtained by a nonlinear least squares regression analysis on the basis of a one binding site model.

5-HT$_1$ Functional Assay (cAMP)

CHO/5-HT$_{1A}$ cells were random seeded at a density of about 200,000/well in 24 well plates the day prior to the experiment. On the day of the experiment, cells were pretreated for 15 minutes at 37° C. with 500 μM isobutyl-methylxantine (IBMX) dissolved in culture medium without serum. Wells were then divided in different groups in duplicate as follows: control, 10 μM FSK, 10 μM FSK+1 μM 5-HT as positive standard and 10 μM FSK+10 μM of the different compound under evaluation. Sample solutions were added and incubated for additional 15 minutes at 37° C. After incubation, the medium was aspirated and the reaction stopped by adding 200 μl of lysis buffer. Plates were shaken for 5 minutes, then the lysate was removed and samples were stored at 4° C. until the day of the assay. For the cAMP evaluation, samples were properly diluted and the cAMP content was measured by an enzyme immunoassay system.

Data Analysis:

Results are expressed as % inhibition of the cAMP accumulation induced by 10 μM FSK.

D$_4$ Radioligand Receptor Binding Assay

Membranes from CHO cells expressing D$_4$ human receptors, were suspended in incubation buffer.

Binding Assay:

Binding assays were performed in MultiProbe 204 pipetting system (Packard), according to a predetermined mapping, consistent with the software Screen. The compounds were tested in singlicate at one concentration ($10^{-7}$ M) in a total volume of 1000 μl (980 μl of diluted membranes, 10 μl DMSO or unlabelled ligand and 10 μl of [$^3$H] YM-09151-2 (0.15–0.25 nM). After incubation for 120 minutes at 27° C., the reaction was stopped by rapid filtration through Tomtec Cell Harvester (48 wells) using Filtermat B (presoaked in 0.1% PEI) filters. Filters were washed with ice-cold 50 mM Tris-HCl (pH 7.4) buffer (9×700 μl), dried, covered with MeltiLex B/HS (Wallac) scintillator sheets and heated in oven at 80° C. to 90° C. for about 10 minutes, transferred into plastic sample bags (Wallac), sealed, and put into 1024 Beta Plate scintillation counter (Wallac). Non-specific binding was determined in the presence of clozapine dissolved in DMSO to a final concentration of $10^{-5}$ M.

Data Analysis:

The specific radioligand binding to the receptor was defined by the difference between total binding and non-specific binding, determined in the presence of an excess of unlabelled ligand. Results were expressed as percentage of control specific binding obtained in the presence of the compounds.

5-HT$_{2A}$ Radioligand Receptor Binding Assay

Tissue Preparation:

Rats (male Sprague-Dawley, 200–250 g) were used. Cerebral frontal cortex was homogenized in 10 volumes of ice cold 0.32 M sucrose in 5 mM Tris-HCl (pH 74) buffer. After centrifugation of the homogenate (1,000×g for 10 minutes) the supernatant was then recentrifuged at 48,000×g for 15 minutes. The resulting pellet was gently homogenized in an equal volume of 50 mM Tris-HCl buffer (pH 7.4) and incubated at 37° C. for 10 minutes. Membranes were then collected by centrifugation as above described and finally resuspended in 10 volumes of 50 mM Tris-HCl buffer (pH 7.4).

Binding Assay:

For displacement experiments membranes (980 µl) were diluted in 50 mM Tris-HCl buffer (pH 7.4) to a final concentration of 1:100 (w/v); the tissue suspension was then incubated at 37° C. for 10 minutes in a final volume of 1 ml in the presence of 0.5 nM [$^3$H]-Ketanserin. Non-specific binding was determined by incubating similar samples with unlabelled methysergide (100 µM). After incubation, samples prepared in a 24 wells cell culture cluster (Costar) were rapidly filtered by Inotech Cell Harvester (IH 201 filters). The filters were washed three times with 2 ml ice-cold Tris-HCl buffer and placed in polyethylene vials, then 4 ml of Filter Count scintillation cocktail (Packard) were added. The radioactivity present was counted by liquid scintillation spectrometry.

Data Analysis:

The affinity values (IC$_{50}$) for the compounds were obtained by a nonlinear least squares regression analysis on the basis of a one binding site model.

5-H T$_2$ Functional Assay (PI Turnover)

Tissue Preparation:

Cross-chopped miniprisms (350×350 µm) were prepared from mouse whole cerebral cortices and incubated for 60 minutes at 37° C. in Krebs-Henseleit buffer containing 2 g/l glucose.

Functional Assay:

Cerebral cortex miniprisms were distributed in vials and incubated for 30 minutes with approximately 170 nM [$^3$H]-myoinositol (10–20 Ci/mmol) and 10 nM lithium chloride. Samples were divided in different groups in triplicate: control, 100 µM 5-HT, 10 and 30 µM flibanserin+100 µM 5-HT, as standards, and 10 µM of the different compound under investigation+100 µM 5-HT. When 5-HT was added the incubation continued for 45 minutes. Compounds under investigation and flibanserin were added 10 minutes before dispensing 5-HT. Incubation was terminated by the addition of 940 µl chloroform-methanol (1:2 v/v). Further aliquots of chloroform (310 µl) and water (310 µl) were added and labeled inositol phosphates (1 Ps) were extracted from the aqueous phase by ion exchange chromatography using Dowex resin in the formate form. After addition of 10 ml of PicoFluor 40 scintillation cocktail (Packard), the radioactivity present in an aliquot (400 µl) of the aqueous extract was counted by liquid scintillation spectrometry.

Data Analysis:

Results are expressed as % inhibition of the PI turnover accumulation induced by 100 µM 5-HT.

The following Tables 4 to 6 collect the biological data at the receptors of the new compounds.

TABLE 4

| % Inhibition at 5-HT$_{1A}$ and D$_4$ Receptors | | | | | |
|---|---|---|---|---|---|
| Comp. No. | 5-HT$_{1A}$ Receptor Binding Assay % inhibition ($10^{-7}$ M) | D$_4$ Receptor Binding Assay % inhibition ($10^{-7}$ M) | Comp. No. | 5-HT$_{1A}$ Receptor Binding Assay % inhibition ($10^{-7}$ M) | D$_4$ Receptor Binding Assay % inhibition ($10^{-7}$ M) |
| 1 | 56 | 38 | 78 | 69 | 44 |
| 5 | 92 | 54 | 79 | 86 | 58 |
| 7 | 77 | 91 | 81 | 55 | 78 |
| 9 | 93 | 32 | 83 | 89 | 39 |
| 10 | 60 | 47 | 84 | 52 | 42 |
| 11 | 48 | 90 | 85 | 77 | 79 |
| 19 | 69 | 32 | 92 | 94 | 55 |
| 20 | 50 | 60 | 93 | 94 | 62 |
| 23 | 73 | 48 | 94 | 88 | 72 |
| 24 | 90 | 67 | 95 | 85 | 64 |
| 25 | 48 | 44 | 96 | 92 | 72 |
| 26 | 70 | 94 | 107 | 55 | 58 |
| 28 | 89 | 35 | 118 | 80 | 36 |
| 29 | 57 | 83 | 145 | 85 | 42 |
| 30 | 44 | 90 | 149 | 88 | 35 |
| 37 | 90 | 54 | 150 | 57 | 52 |
| 38 | 92 | 78 | 158 | 95 | 72 |
| 39 | 36 | 42 | 159 | 85 | 50 |
| 43 | 104 | 55 | 164 | 96 | 41 |
| 45 | 100 | 82 | 169 | 85 | 58 |
| 56 | 63 | 71 | 177 | 98 | 39 |
| 59 | 75 | 51 | 182 | 62 | 45 |
| 60 | 93 | 82 | 183 | 96 | 62 |
| 62 | 73 | 96 | 187 | 94 | 36 |
| 64 | 92 | 43 | 188 | 78 | 78 |
| 65 | 52 | 74 | 189 | 54 | 99 |
| 66 | 65 | 99 | 197 | 77 | 43 |
| 73 | 91 | 58 | 215 | 98 | 48 |
| 74 | 92 | 62 | 216 | 92 | 44 |
| 75 | 67 | 54 | 219 | 89 | 37 |
| 224 | 98 | 51 | 332 | 78 | 85 |
| 226 | 71 | 32 | 333 | 99 | 80 |
| 228 | 95 | 33 | 335 | 95 | 55 |
| 229 | 67 | 34 | 336 | 90 | 81 |
| 241 | 69 | 32 | 348 | 99 | 51 |
| 254 | 85 | 34 | 349 | 73 | 31 |
| 255 | 58 | 33 | 361 | 86 | 46 |
| 256 | 59 | 51 | 364 | 77 | 36 |
| 263 | 92 | 42 | 365 | 89 | 63 |
| 265 | 55 | 78 | 367 | 61 | 90 |
| 280 | 93 | 38 | 369 | 96 | 59 |
| 282 | 53 | 77 | 370 | 93 | 60 |
| 285 | 96 | 32 | 371 | 59 | 95 |
| 286 | 65 | 87 | 378 | 77 | 35 |
| 293 | 89 | 32 | 382 | 88 | 39 |
| 297 | 96 | 34 | 395 | 86 | 32 |
| 303 | 71 | 70 | 399 | 82 | 32 |
| 310 | 85 | 49 | 404 | 95 | 34 |
| 311 | 59 | 60 | 412 | 93 | 39 |
| 314 | 93 | 82 | 416 | 96 | 39 |
| 316 | 72 | 94 | 446 | 92 | 31 |
| 318 | 92 | 36 | 501 | 70 | 63 |
| 319 | 94 | 70 | 504 | 93 | 34 |
| 327 | 78 | 74 | 505 | 78 | 58 |
| 330 | 97 | 84 | 527 | 73 | 36 |
| 331 | 100 | 92 | 535 | 97 | 39 |

TABLE 5

5-HT$_{1A}$ Agonist Activity

| Compound No. | 5-HT$_{1A}$ Receptor Binding IC$_{50}$ (nM) | cAMP % inhibition |
|---|---|---|
| 5 | 13 | 63 |
| 9 | 9.9 | 48 |
| 37 | 16 | 44 |
| 60 | 6.2 | 65 |
| 64 | 12 | 52 |
| 73 | 13 | 45 |
| 83 | 15 | 64 |
| 158 | 13 | 48 |
| 164 | 4.2 | 73 |
| 168 | 5.0 | 71 |
| 177 | 3.3 | 76 |
| 183 | 7.2 | 66 |
| 187 | 8.2 | 44 |
| 202 | 1.7 | 72 |
| 206 | 2.1 | 80 |
| 215 | 0.85 | 83 |
| 217 | 5.2 | 68 |
| 219 | 15 | 61 |
| 228 | 6.0 | 82 |
| 254 | 7.4 | 66 |
| 263 | 8.8 | 63 |
| 284 | 4.9 | 82 |
| 285 | 5.2 | 47 |
| 296 | 8.2 | 82 |
| 297 | 7.9 | 74 |
| 301 | 2.6 | 83 |
| 310 | 15 | 63 |
| 314 | 7.1 | 44 |
| 318 | 3.1 | 61 |
| 330 | 7.9 | 62 |
| 333 | 16 | 67 |
| 335 | 3.5 | 69 |
| 347 | 13 | 65 |
| 348 | 3.5 | 57 |
| 352 | 4.1 | 79 |
| 365 | 15 | 82 |
| 369 | 3.5 | 84 |
| 370 | 4.4 | 52 |
| 381 | 44 | 79 |
| 382 | 11 | 64 |
| 386 | 6.7 | 82 |
| 403 | 5.5 | 84 |
| 404 | 2.1 | 60 |
| 415 | 14 | 82 |
| 416 | 7.9 | 77 |
| 420 | 1.8 | 87 |
| 421 | 0.66 | 56 |
| 446 | 7.3 | 81 |
| 459 | 8.8 | 86 |
| 468 | 3.1 | 66 |
| 472 | 3.1 | 67 |
| 481 | 11 | 82 |
| 499 | 5.0 | 74 |
| 503 | 2.8 | 87 |
| 504 | 3.6 | 50 |
| 512 | 0.59 | 68 |
| 514 | 7.9 | 67 |
| 520 | 8.1 | 70 |
| 521 | 0.61 | 67 |
| 525 | 1.5 | 87 |
| 536 | 9.5 | 55 |

TABLE 6

5-HT$_{2A}$ Antagonist Activity

| Compound No. | 5-HT$_{2A}$ Receptor Binding IC$_{50}$ (nM) | PI Turnover % inhibition |
|---|---|---|
| 9 | 16 | 45 |
| 73 | 0.90 | 42 |
| 83 | 43 | 86 |
| 168 | 46 | 22.00 |
| 177 | 7.7 | 39 |
| 183 | 27 | 12.00 |
| 206 | 17 | 90 |
| 215 | 3.2 | 83 |
| 254 | 65 | 64 |
| 514 | 74 | 41 |
| 521 | 30 | 48 |

We claim:

1. A compound of formula (I)

$$\text{(I)}$$

wherein:

$R^1$ is $C_1$–$C_6$-alkyl substituted by a group selected from $C_1$–$C_6$-alkoxy, —OCONHC$_1$–C$_6$-alkyl, —NHSO$_2$C$_1$–C$_6$-alkyl, and —NHCOC$_1$–C$_6$-alkyl;

$R^2$ and $R^3$ together with the nitrogen form a saturated or unsaturated 5- or 6-membered heterocyclic ring optionally containing nitrogen or oxygen as an additional heteroatom, the heterocyclic ring thereof substituted by a group selected from phenyl, benzyl, and diphenylmethyl, each of these groups optionally mono- or di-substituted by one or two groups selected from CF$_3$, C$_1$–C$_4$-alkyl, C$_1$–C$_4$-alkoxy, phenyl, benzyl, halogen, and OH, or $R^2$ and $R^3$ together with the nitrogen form a saturated or unsaturated 5- or 6-membered heterocyclic ring optionally containing nitrogen or oxygen as an additional heteroatom, the heterocyclic ring thereof linked via a single bond, a methylene-bridge, or spiro-connected to a saturated or unsaturated heterocyclic group containing one or two heteroatoms selected from oxygen and nitrogen, the heterocyclic group optionally mono- or di-substituted by a group selected from CF$_3$, C$_1$–C$_4$-alkyl, C$_1$–C$_4$-alkoxy, phenyl, benzyl, halogen, =O, and OH, or $R^2$ and $R^3$ together with the nitrogen form a saturated or unsaturated bi- or tricyclic heterocyclic ring-system optionally containing nitrogen or oxygen as an additional heteroatom, the heterocyclic ring-system being optionally substituted by a group selected from CF$_3$, C$_1$–C$_4$-alkyl, C$_1$–C$_4$-alkoxy, phenyl, benzyl, halogen, =O, and OH; and A is $C_1$–$C_6$-alkylene, $C_2$–$C_6$-alkenylene, or $C_2$–$C_6$-alkynylene, or a pharmaceutically acceptable salt thereof.

2. The compound of formula (I) according to claim 1, wherein:

$R^1$ is $C_1$–$C_4$-alkyl substituted by a group selected from $C_1$–$C_4$-alkoxy, —OCONH$C_1$–$C_4$-alkyl, —OCONH$C_1$–$C_4$-alkyl, —NHSO$_2C_1$–$C_4$-alkyl, and —NHCO$C_1$–$C_4$-alkyl;

$R^2$ and $R^3$ together with the nitrogen form a saturated or unsaturated 5- or 6-membered heterocyclic ring optionally containing nitrogen as an additional heteroatom, the heterocyclic ring thereof substituted by a group selected from phenyl, benzyl, diphenylmethyl, pyridinyl, pyrimidinyl, benzimidazolonyl, and 3,4-methylenedioxibenzyl, each of these groups optionally mono- or di-substituted by a group selected from $CF_3$, $C_1$–$C_4$-alkyl, $C_1$–$C_4$-alkoxy, halogen, and OH; and A is $C_1$–$C_4$-alkylene or $C_2$–$C_4$-alkenylene, or a pharmaceutically acceptable salt thereof.

3. The compound of formula (I) according to claim 1, wherein:

$R^1$ is ethyl substituted by a group selected from —OCH$_3$, OCH$_2$CH$_3$, —OCONHCH$_3$, —OCONHCH$_2$CH$_3$, —NHSO$_2$CH$_3$, and —NHSO$_2$CH$_2$CH$_3$;

$R^2$ and $R^3$ together with the nitrogen form a 6-membered saturated or unsaturated heterocyclic ring optionally containing nitrogen as an additional heteroatom, the heterocyclic ring thereof substituted by a group selected from phenyl, pyridinyl, pyrimidinyl, benzimidizalonyl, and phenyl mono- or di-substituted by a group selected from $CF_3$, $CH_3$, $OCH_3$, F, and Cl;

A is $C_1$–$C_4$-alkylene or $C_2$–$C_4$-alkenylene, or a pharmaceutically acceptable salt thereof.

4. The compound of formula (I) according to claim 1, wherein:

$R^1$ is ethyl substituted by a group selected from —OCH$_3$, —OCONHCH$_2$CH$_3$, and —NHSO$_2$CH$_3$;

$R^2$ and $R^3$ together with the nitrogen form a 6-membered saturated or unsaturated heterocyclic ring optionally containing nitrogen as an additional heteroatom, the heterocyclic ring thereof substituted by a group selected from pyridinyl, phenyl, and phenyl mono- or di-substituted by a group selected from $CF_3$, $CH_3$, $OCH_3$, F, and Cl; and A is ethylene, propylene, butylene, or butenylene, or a pharmaceutically acceptable salt thereof.

5. The compound of formula (I) according to claim 1, wherein:

$R^1$ is ethyl substituted by a group selected from —OCH$_3$, —OCONHCH$_2$CH$_3$, and —NHSO$_2$CH$_3$;

$R^2$ and $R^3$ together with the nitrogen form a heterocyclic ring selected from the group consisting of piperazine, piperidine, and tetrahydropyridine, the heterocyclic ring thereof substituted by a group selected from pyridinyl, phenyl, and phenyl mono- or di-substituted by a group selected from $CF_3$, $CH_3$, and Cl; and A is ethylene, butylene, or butenylene, or a pharmaceutically acceptable salt thereof.

6. A compound of formula (I)

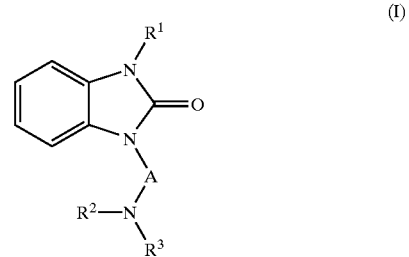

wherein:

$R^1$ is ethyl substituted by a group selected from OH, OCH$_3$, —OCONHCH$_2$CH$_3$, and —NHSO$_2$CH$_3$;

$R^2$ and $R^3$ together with the nitrogen form a piperazine ring, the piperazine ring thereof substituted by a group selected from trifluoromethylphenyl, methylphenyl, dimethylphenyl, and chlorophenyl; and A is ethylene, butylene, or butenylene, or a pharmaceutically acceptable salt thereof.

7. The compound of formula (I) according to claim 1, wherein $R^1$ is a $C_1$–$C_4$-alkyl group.

8. The compound of formula (I) according to claim 1, wherein A is $C_1$–$C_4$-alkylene, $C_2$–$C_4$-alkenylene, or $C_2$–$C_4$-alkynylene.

9. A compound selected from the group consisting of:

(a) 1-(2-methoxyethyl)-3-(4-{4-[3-(trifluoromethyl)phenyl]-1-piperazinyl}butyl)-1,3-dihydro-2H-benzimidazol-2-one;

(b) 2-[2-oxo-3-(4-{4-[3-(trifluoromethyl)phenyl]-1-piperazinyl}butyl)-2,3-dihydro-1H-benzimidazol-1-yl]ethyl-ethylcarbamate;

(c) 1-(2-methoxyethyl)-3-(2-{4-[3-(trifluoromethyl)phenyl]-1-piperazinyl}ethyl)-1,3-dihydro-2H-benzimidazol-2-one;

(d) 1-{2-[4-(2,3-dimethylphenyl)-1-piperazinyl]ethyl}-3-(2-methoxyethyl)-1,3-dihydro-2H-benzimidazol-2-one;

(e) 2-[2-oxo-3-(2-{4-[3-(trifluoromethyl)phenyl]-1-piperazinyl}ethyl)-2,3-dihydro-1H-benzimidazol-1-yl]ethyl-ethylcarbamate;

(f) 2-(3-{2-[4-(2,3-dimethylphenyl)-1-piperazinyl]ethyl}-2-oxo-2,3-dihydro-1H-benzimidazol-1-yl)ethyl-ethylcarbamate;

(g) N-[2-(3-{2-[4-(2,3-dimethylphenyl)-1-piperazinyl]ethyl}-2-oxo-2,3-dihydro-1H-benzimidazol-1-yl)ethyl]methanesulfonamide;

(h) N-[2-(3-{(2Z)-4-[4-(3-methylphenyl)-1-piperazinyl]-2-butenyl}-2-oxo-2,3-dihydro-1H-benzimidazol-1-yl)ethyl]methanesulfonamide; and (i) N-[2-(3-{(2E)-4-[4-(3-chlorophenyl)-1-piperazinyl]-2-butenyl}-2-butenyl}-2-oxo-2,3-dihydro-1H-benzimidazol-1-yl)ethyl]methanesulfonamide, or a pharmaceutically acceptable salt thereof.

10. 1-{4-[4-(2,3-dimethylphenyl)-1-piperazinyl]butyl}-3-(2-hydroxyethyl)-1,3-dihydro-2H-benzimidazol-2-one, or a pharmaceutically acceptable salt thereof.

11. 1-{2-[4-(3-chlorophenyl)-1-piperazinyl]ethyl}-3-(2-hydroxyethyl)-1,3-dihydro-2H-benzimidazol-2-one, or a pharmaceutically acceptable salt thereof.

12. A pharmaceutical composition comprising an effective amount of a compound of formula (I) according to one of claims 1 to 9 and a pharmaceutical carrier, diluent, or excipient.

13. A method for treatment of anxiety disorders and affective disorders, in a host in need of such treatment, which method comprises administering the host an effective amount of a compound according to one of claims 1 to 9.

14. A method for treatment of a disease selected from the group consisting of depression, psychosis, schizophrenia, eating disorders, sexual disorders, Parkinson's disease, and stroke and traumatic brain injury, in a host in need of such treatment, which method comprises administering the host an effective amount of a compound according to one of claims 1 to 9.

* * * * *